US006294652B1

(12) United States Patent
Biswas et al.

(10) Patent No.: US 6,294,652 B1
(45) Date of Patent: Sep. 25, 2001

(54) RESPONSE REGULATOR

(75) Inventors: Sanjoy Biswas, Paoli; James Yigong Ge, Royersford; David John Holmes, West Chester; Karen A Ingraham, Auburn; John Throup, Royersford; Nicola Gail Wallis, Wayne; Magdalena Zalacain, West Chester, all of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/487,370

(22) Filed: Jan. 18, 2000

Related U.S. Application Data

(62) Division of application No. 09/139,064, filed on Aug. 25, 1998.
(60) Provisional application No. 60/060,714, filed on Sep. 9, 1997.
(51) Int. Cl.[7] .............................. C01K 1/00; A61K 38/00; G01N 31/00; A01N 37/18
(52) U.S. Cl. .................... 530/350; 530/300; 435/69.1; 436/15; 436/86; 514/2; 514/12; 930/10

(58) Field of Search ..................................... 530/300, 350; 435/69.1; 436/15, 86; 514/2, 12; 930/10

(56) References Cited

PUBLICATIONS

SwissProt Submission, Accession No. P13800, Direct Submission, Jan. 1, 1990.

Henner, et al., "Localization of *Bacillus subtilis* sacU(Hy) Mutations to Two Linked Genes with Similarities to the Conserved Procaryotic Family of Two–Component Signalling Systems", *Journal of Bacteriology*, vol. 170, No. 11, pp. 5102–5109, Nov. 1988.

*Primary Examiner*—John S. Brusca
*Assistant Examiner*—Stephen Siu
(74) *Attorney, Agent, or Firm*—Edward R. Gimmi; Thomas S. Deibert; William T. King

(57) ABSTRACT

The invention provides Response regulator polypeptides and polynucleotides encoding Response regulator polypeptides and methods for producing such polypeptides by recombinant techniques. Also provided are methods for utilizing Response regulator polypeptides to screen for antibacterial compounds.

22 Claims, No Drawings

SEQUENCE LISTING

```
<160> NUMBER OF SEQ ID NOS: 9

<210> SEQ ID NO 1
<211> LENGTH: 3453
<212> TYPE: DNA
<213> ORGANISM: Streptococcus pneumoniae
<220> FEATURE:
<221> NAME/KEY: CDS
<222> LOCATION: (2144)...(3427)

<400> SEQUENCE: 1
cttatatgca gaacatggtt atagctttcg ggaatacagt ttgaaggagg cttggtctct      60
ttacaagcaa aattttatct caagcaacct gattttctat agcttttttag gtgtgggtct    120 agttttgacc tatggtttgt atctcttggt gcaattgcct catcagacca ttgttcattt    180
gattgcgacc cttttgaatg tcctagtagt tgccctgatc tttttggctt atacagtatc    240
tttaaaatta caagtttatt ttgccttgtc ctatcgaaat agtctcaaat tatccttgat    300
tggcatcttt atgagtctag cagctgtggc taaggttctc cttgggactg tgctacttgt    360
agcaattggt tactatatgc ctgccctgct attttttgta ggaattggga tgtggcattt    420
ctttatcagt gatatgttgg aacctgtcta tgaaatcatc catgaaaaat tggcgacaaa    480
atagaatgaa gcacttttgg ctacatacgc ttctaagaac ctatagttca gtgatgatca    540
ttatcattgc gagttttgca atcttactct cttacgctga ctgggattca cgtgaaaagg    600
aagcccagag agtagcccag cgtgtaactg ctagaacagt gagtgaaatt gaatattacc    660
atagagagtc aacccagata gctcaggctt tagttgaaaa ccaagctcgt attgagggaa    720
tctataaata ctttagcctt agcatgccag actatttta ctggcaatta gagcggaaag    780
cttcgcctta tatatcagtc tctctgtatg aaaatgttga tgacctctat gttcgaaatg    840
attttgtaac tggggtggcc attgcttttc aagattacaa ggaagtctat gtttctacta    900
aagacaaacg tagtggagaa aaaatcaggg ctgaggattt caaaccagca ggaaatagtt    960
ttgccattcc agtgtcagat ccagtgtcag atcaagactt aggagtgatt tacatctcct   1020
tggatcctgc tgtttatac catgccattg ataatactag aggtcatact ccgatggcag   1080
taacagtgac cgaaccttttt gatacggaga tttttcatat tggtgagaca gttgataagg   1140
agagtgaaaa ttggctagtt ggcttaactt ctcatggtta tcaggttcag gtggcagttc   1200
```

-continued

```
ccaaaaactt tgttttacaa ggaacggtga ccagctctgc tttgattgtg ggcttgagcc    1260
ttctctttat tgtcattctt tatctgactt tgaggcagac ctttgctaat tatcaaaagc    1320
aggtagtgga tttggtggat tccatccaag ctattgccca aggacaagaa ggtcttcgca    1380
ttgatacgct tgaaaaggat caggaattgc tcctaatcgc ggagacgacc aatgatatgt    1440
tggatcgatt ggaaaagaat atccatgata tttaccagtt agaactcagt caaaagatg     1500 ccaatatgcg ggccttgcag gcgcaaatca atcctcattt tatgtataat acgctggagt    1560
tcttgcgcat gtatgcagtt atgcagagtc aagatgagtt ggcagatatc atttatgaat    1620
tcagtagtct cttgcgtaac aatatttccg acgaaagaga gaccctcctc aaacaggaat    1680
tagaattttg ccgtaaatac agctatctct gcatggttcg ctatcccaag tccattgcct    1740
atggtttcaa gatagatcca gagttagaga atatgaagat tcccaagttt accttgcaac    1800
cgctggtaga aaactatttc gcgcatggtg ttgaccacag gcggacagat aatgtgatta    1860
gcatcaaggc tcttaaacag gatggttttg tggaaatttt ggtggtcgat aatggtagag    1920
gaatgtcggc tgaaaagttg gcaaatatcc gagaaaaatt aagtcagaga tattttgaac    1980
accaagccag ctacagtgat caaaggcagt ctatcgggat tgtcaatgta cacgagcgtt    2040
ttgtgctcta ttttggagac cgctatgcca ttactataga gtctgcagag caagccggtg    2100
ttcagtatcg tattacaatt caagatgagt agaaaggag aaa atg tat aaa gta       2155
                                              Met Tyr Lys Val
                                                1 tta tta gta gat gat gag tac atg gtg aca gaa ggt ctg aag cgt ttg     2203
Leu Leu Val Asp Asp Glu Tyr Met Val Thr Glu Gly Leu Lys Arg Leu
  5              10                  15                  20 att ccc ttt gat aag tgg gat atg gag gtc gtc gca aca gtc agt cat     2251
Ile Pro Phe Asp Lys Trp Asp Met Glu Val Val Ala Thr Val Ser His
             25                  30                  35 gcc gat gaa gct cta gaa tat gtt cag gaa aat cct gtc gat gtc atc     2299
Ala Asp Glu Ala Leu Glu Tyr Val Gln Glu Asn Pro Val Asp Val Ile
         40                  45                  50 att tcc gat gtc aat atg cca gac aaa aca ggg ctt gat atg att cgg     2347
Ile Ser Asp Val Asn Met Pro Asp Lys Thr Gly Leu Asp Met Ile Arg
     55                  60                  65 gag atg aaa gag atc tta cca gat gct gcc tat atc ctg ctc tca ggt     2395
Glu Met Lys Glu Ile Leu Pro Asp Ala Ala Tyr Ile Leu Leu Ser Gly
 70                  75                  80 tat cag gag ttt gat tat gta aaa aga gca atg aat ctt agt gtg gtg     2443
Tyr Gln Glu Phe Asp Tyr Val Lys Arg Ala Met Asn Leu Ser Val Val
 85                  90                  95                 100 gac tat ttg gtc aaa cct gtt gat aag gta gag ctg gga aat ctg ctg     2491
Asp Tyr Leu Val Lys Pro Val Asp Lys Val Glu Leu Gly Asn Leu Leu
                105                 110                 115 gag aag att gca ggt cag ctc ggc gag aga ggg aag aaa agt cag act     2539
Glu Lys Ile Ala Gly Gln Leu Gly Glu Arg Gly Lys Lys Ser Gln Thr
            120                 125                 130 ctt agt caa gaa tta gac gag gct gga ttt gtt agt tat tta ggg gat     2587
Leu Ser Gln Glu Leu Asp Glu Ala Gly Phe Val Ser Tyr Leu Gly Asp
        135                 140                 145 aag gag aat tgg tgg ata ggt cta tcc aag gaa aaa caa ggt tcc ttc     2635
Lys Glu Asn Trp Trp Ile Gly Leu Ser Lys Glu Lys Gln Gly Ser Phe
    150                 155                 160 acc att ccc tac tat gtc ttg ggt caa gcc tgg cag att ttc att tct     2683
Thr Ile Pro Tyr Tyr Val Leu Gly Gln Ala Trp Gln Ile Phe Ile Ser
165                 170                 175                 180 gac caa ccc cta gat ggt tta gtc gtt aca cct ttt gaa gct cct tat     2731
```

```
                -continued

Asp Gln Pro Leu Asp Gly Leu Val Val Thr Pro Phe Glu Ala Pro Tyr
            185                 190                 195 caa gaa cat ttt gaa cgc tgg aag ctg aat gct gag aaa acc ctc ttt    2779
Gln Glu His Phe Glu Arg Trp Lys Leu Asn Ala Glu Lys Thr Leu Phe
            200                 205                 210 tac ggt tct gta aat ctg cag cag tct gag agt ctc ttt gcc tat tac    2827
Tyr Gly Ser Val Asn Leu Gln Gln Ser Glu Ser Leu Phe Ala Tyr Tyr
            215                 220                 225 gaa ccg att tat agg gtt atc att cag gga aat ctc aat caa atc gta    2875
Glu Pro Ile Tyr Arg Val Ile Ile Gln Gly Asn Leu Asn Gln Ile Val
            230                 235                 240 gaa gag tta aat ctc ttg gag aag gta gtt ctt gaa aat acg ccg cga    2923
Glu Glu Leu Asn Leu Leu Glu Lys Val Val Leu Glu Asn Thr Pro Arg
245                 250                 255                 260 att ccg att act aaa cag ctt ttt atc cag ttt gtc atg gat gtc ttc    2971
Ile Pro Ile Thr Lys Gln Leu Phe Ile Gln Phe Val Met Asp Val Phe
            265                 270                 275 cat tta ttt gaa cat ctc aaa gct gat gat atg acg gac att gtc aaa    3019
His Leu Phe Glu His Leu Lys Ala Asp Asp Met Thr Asp Ile Val Lys
            280                 285                 290 acc att cat gct att caa tcc ttc gat gaa ttg gtt tct tat atc aag    3067
Thr Ile His Ala Ile Gln Ser Phe Asp Glu Leu Val Ser Tyr Ile Lys
            295                 300                 305 gaa act ctg atc agc ttt ttc ggt caa tac cgt atg aat gaa aat gtg    3115
Glu Thr Leu Ile Ser Phe Phe Gly Gln Tyr Arg Met Asn Glu Asn Val
            310                 315                 320 gtc agt gtg ctg gaa gtc att ggt cgt gat tac caa aaa gag ctt tcc    3163
Val Ser Val Leu Glu Val Ile Gly Arg Asp Tyr Gln Lys Glu Leu Ser
325                 330                 335                 340 ctc aag gat atc agt aag gcc ctc ttt atc aat cct gtc tat cta ggg    3211
Leu Lys Asp Ile Ser Lys Ala Leu Phe Ile Asn Pro Val Tyr Leu Gly
            345                 350                 355 cag ttg att aag cgt gaa acc gat tcg acc ttt gca gag tta cta aac    3259
Gln Leu Ile Lys Arg Glu Thr Asp Ser Thr Phe Ala Glu Leu Leu Asn
            360                 365                 370 aaa caa cgt att aag gct gcc caa caa ctt ttg ctt tca act agt gac    3307
Lys Gln Arg Ile Lys Ala Ala Gln Gln Leu Leu Leu Ser Thr Ser Asp
            375                 380                 385 agc atc gaa aat att tgt tat gct gtt ggt tac agt aac ctt gga tat    3355
Ser Ile Glu Asn Ile Cys Tyr Ala Val Gly Tyr Ser Asn Leu Gly Tyr
            390                 395                 400 ttc tat aaa gtt ttc cga aaa ttg tgc gga aaa tcg cca aaa gcc tac    3403
Phe Tyr Lys Val Phe Arg Lys Leu Cys Gly Lys Ser Pro Lys Ala Tyr
405                 410                 415                 420 cga aaa cag gta gaa act ata cta taagatttgt attcctttac aaaatg       3453
Arg Lys Gln Val Glu Thr Ile Leu
            425

<210> SEQ ID NO 2
<211> LENGTH: 428
<212> TYPE: PRT
<213> ORGANISM: Streptococcus pneumoniae

<400> SEQUENCE: 2

Met Tyr Lys Val Leu Leu Val Asp Asp Glu Tyr Met Val Thr Glu Gly
1               5                   10                  15

Leu Lys Arg Leu Ile Pro Phe Asp Lys Trp Asp Met Glu Val Val Ala
            20                  25                  30

Thr Val Ser His Ala Asp Glu Ala Leu Glu Tyr Val Gln Glu Asn Pro
        35                  40                  45
```

-continued

Val Asp Val Ile Ile Ser Asp Val Asn Met Pro Asp Lys Thr Gly Leu
    50                  55                  60

Asp Met Ile Arg Glu Met Lys Glu Ile Leu Pro Asp Ala Ala Tyr Ile
65                  70                  75                  80

Leu Leu Ser Gly Tyr Gln Glu Phe Asp Tyr Val Lys Arg Ala Met Asn
                85                  90                  95

Leu Ser Val Val Asp Tyr Leu Val Lys Pro Val Asp Lys Val Glu Leu
                100                 105                 110

Gly Asn Leu Leu Glu Lys Ile Ala Gly Gln Leu Gly Glu Arg Gly Lys
            115                 120                 125

Lys Ser Gln Thr Leu Ser Gln Glu Leu Asp Glu Ala Gly Phe Val Ser
    130                 135                 140

Tyr Leu Gly Asp Lys Glu Asn Trp Trp Ile Gly Leu Ser Lys Glu Lys
145                 150                 155                 160

Gln Gly Ser Phe Thr Ile Pro Tyr Tyr Val Leu Gly Ala Trp Gln
                165                 170                 175

Ile Phe Ile Ser Asp Gln Pro Leu Asp Gly Leu Val Val Thr Pro Phe
                180                 185                 190

Glu Ala Pro Tyr Gln Glu His Phe Glu Arg Trp Lys Leu Asn Ala Glu
                195                 200                 205

Lys Thr Leu Phe Tyr Gly Ser Val Asn Leu Gln Gln Ser Glu Ser Leu
    210                 215                 220

Phe Ala Tyr Tyr Glu Pro Ile Tyr Arg Val Ile Ile Gln Gly Asn Leu
225                 230                 235                 240

Asn Gln Ile Val Glu Glu Leu Asn Leu Leu Glu Lys Val Val Leu Glu
                245                 250                 255

Asn Thr Pro Arg Ile Pro Ile Thr Lys Gln Leu Phe Ile Gln Phe Val
                260                 265                 270

Met Asp Val Phe His Leu Phe Glu His Leu Lys Ala Asp Asp Met Thr
                275                 280                 285

Asp Ile Val Lys Thr Ile His Ala Ile Gln Ser Phe Asp Glu Leu Val
            290                 295                 300

Ser Tyr Ile Lys Glu Thr Leu Ile Ser Phe Phe Gly Gln Tyr Arg Met
305                 310                 315                 320

Asn Glu Asn Val Val Ser Val Leu Glu Val Ile Gly Arg Asp Tyr Gln
                325                 330                 335

Lys Glu Leu Ser Leu Lys Asp Ile Ser Lys Ala Leu Phe Ile Asn Pro
            340                 345                 350

Val Tyr Leu Gly Gln Leu Ile Lys Arg Glu Thr Asp Ser Thr Phe Ala
    355                 360                 365

Glu Leu Leu Asn Lys Gln Arg Ile Lys Ala Ala Gln Gln Leu Leu Leu
370                 375                 380

Ser Thr Ser Asp Ser Ile Glu Asn Ile Cys Tyr Ala Val Gly Tyr Ser
385                 390                 395                 400

Asn Leu Gly Tyr Phe Tyr Lys Val Phe Arg Lys Leu Cys Gly Lys Ser
                405                 410                 415

Pro Lys Ala Tyr Arg Lys Gln Val Glu Thr Ile Leu
            420                 425

<210> SEQ ID NO 3
<211> LENGTH: 3453
<212> TYPE: DNA
<213> ORGANISM: Streptococcus pneumoniae -continued

```
<400> SEQUENCE: 3
cttatatgca gaacatggtt atagctttcg ggaatacagt ttgaaggagg cttggtctct      60
ttacaagcaa aatttatct caagcaacct gattttctat agcttttag gtgtgggtct      120 agttttgacc tatggtttgt atctcttggt gcaattgcct catcagacca ttgttcattt     180
gattgcgacc cttttgaatg tcctagtagt tgccctgatc tttttggctt atacagtatc     240
tttaaaatta caagtttatt ttgccttgtc ctatcgaaat agtctcaaat tatccttgat     300
tggcatcttt atgagtctag cagctgtggc taaggttctc cttgggactg tgctacttgt     360
agcaattggt tactatatgc ctgccctgct atttttgta ggaattggga tgtggcattt      420
ctttatcagt gatatgttgg aacctgtcta tgaaatcatc catgaaaaat tggcgacaaa     480
atagaatgaa gcacttttgg ctacatacgc ttctaagaac ctatagttca gtgatgatca     540
ttatcattgc gagttttgca atcttactct cttacgctga ctgggattca cgtgaaaagg     600
aagcccagag agtagcccag cgtgtaactg ctagaacagt gagtgaaatt gaatattacc     660
atagagagtc aacccagata gctcaggctt tagttgaaaa ccaagctcgt attgagggaa     720
tctataaata ctttagcctt agcatgccag actattttta ctggcaatta gagcggaaag     780
cttcgcctta tatatcagtc tctctgtatg aaaatgttga tgacctctat gttcgaaatg     840 atttttgtaac tggggtggcc attgctttc aagattacaa ggaagtctat gtttctacta     900
aagacaaacg tagtggagaa aaaatcaggg ctgaggattt caaaccagca ggaaatagtt     960
ttgccattcc agtgtcagat ccagtgtcag atcaagactt aggagtgatt tacatctcct    1020
tggatcctgc tgttttatac catgccattg ataatactag aggtcatact ccgatggcag    1080
taacagtgac cgaaccttt gatacggaga tttttcatat tggtgagaca gttgataagg     1140
agagtgaaaa ttggctagtt ggcttaactt ctcatggtta tcaggttcag gtggcagttc    1200
ccaaaaactt tgttttacaa ggaacggtga ccagctctgc tttgattgtg ggcttgagcc    1260
ttctctttat tgtcattctt tatctgactt tgaggcagac cttgctaat tatcaaaagc     1320 aggtagtgga tttggtggat ccatccaag ctattgccca aggacaagaa ggtcttcgca    1380
ttgatacgct tgaaaaggat caggaattgc tcctaatcgc ggagacgacc aatgatatgt    1440
tggatcgatt ggaaaagaat atccatgata tttaccagtt agaactcagt caaaaagatg    1500
ccaatatgcg ggccttgcag gcgcaaatca atcctcattt tatgtataat acgctggagt    1560
tcttgcgcat gtatgcagtt atgcagagtc aagatgagtt ggcagatatc atttatgaat    1620
tcagtagtct cttgcgtaac aatatttccg acgaaagaga gaccctcctc aaacaggaat    1680
tagaattttg ccgtaaatac agctatctct gcatggttcg ctatcccaag tccattgcct    1740
atggtttcaa gatagatcca gagttagaga atatgaagat tcccaagttt accttgcaac    1800
cgctggtaga aaactatttc gcgcatggtg ttgaccacag gcggacagat aatgtgatta    1860
gcatcaaggc tcttaaacag gatggttttg tggaaattt ggtggtcgat aatggtagag    1920
gaatgtcggc tgaaaagttg gcaaatatcc gagaaaaatt aagtcagaga tattttgaac    1980
accaagccag ctacagtgat caaaggcagt ctatcgggat tgtcaatgta cacgagcgtt    2040
ttgtgctcta ttttggagac cgctatgcca ttactataga gtctgcagag caagccggtg    2100
ttcagtatcg tattacaatt caagatgagt agaaagggag aaaatgtata aagtattatt    2160
agtagatgat gagtacatgg tgacagaagg tctgaagcgt ttgattccct ttgataagtg    2220
ggatatggag gtcgtcgcaa cagtcagtca tgccgatgaa gctctagaat atgttcagga    2280
aaatcctgtc gatgtcatca tttccgatgt caatatgcca gacaaaacag ggcttgatat    2340
```

-continued

```
gattcgggag atgaaagaga tcttaccaga tgctgcctat atcctgctct caggttatca  2400
ggagtttgat tatgtaaaaa gagcaatgaa tcttagtgtg gtggactatt tggtcaaacc  2460
tgttgataag gtagagctgg gaaatctgct ggagaagatt gcaggtcagc tcggcgagag  2520
agggaagaaa agtcagactc ttagtcaaga attagacgag gctggatttg ttagttattt  2580 agggataag gagaattggt ggataggtct atccaaggaa aaacaaggtt ccttcaccat   2640
tccctactat gtcttgggtc aagcctggca gattttcatt tctgaccaac ccctagatgg  2700
tttagtcgtt acacctttg aagctcctta tcaagaacat tttgaacgct ggaagctgaa   2760
tgctgagaaa accctctttt acggttctgt aaatctgcag cagtctgaga gtctctttgc  2820
ctattacgaa ccgatttata gggttatcat tcagggaaat ctcaatcaaa tcgtagaaga  2880
gttaaatctc ttggagaagg tagttcttga aaatacgccg cgaattccga ttactaaaca  2940 gcttttatc cagtttgtca tggatgtctt ccatttattt gaacatctca agctgatga   3000 tatgacggac attgtcaaaa ccattcatgc tattcaatcc ttcgatgaat tggtttctta  3060
tatcaaggaa actctgatca gcttttcgg tcaataccgt atgaatgaaa atgtggtcag   3120
tgtgctggaa gtcattggtc gtgattacca aaaagagctt ccctcaagg atatcagtaa   3180 ggccctcttt atcaatcctg tctatctagg gcagttgatt aagcgtgaaa ccgattcgac  3240
ctttgcagag ttactaaaca aacaacgtat taaggctgcc caacaacttt tgctttcaac  3300
tagtgacagc atcgaaaata tttgttatgc tgttggttac agtaaccttg gatatttcta  3360
taaagttttc cgaaaattgt gcggaaaatc gccaaaagcc taccgaaaac aggtagaaac  3420
tatactataa gatttgtatt cctttacaaa atg                               3453
```

<210> SEQ ID NO 4
<211> LENGTH: 428
<212> TYPE: PRT
<213> ORGANISM: Streptococcus pneumoniae

<400> SEQUENCE: 4

```
Met Tyr Lys Val Leu Leu Val Asp Asp Glu Tyr Met Val Thr Glu Gly
  1               5                  10                  15

Leu Lys Arg Leu Ile Pro Phe Asp Lys Trp Asp Met Glu Val Val Ala
                 20                  25                  30

Thr Val Ser His Ala Asp Glu Ala Leu Glu Tyr Val Gln Glu Asn Pro
             35                  40                  45

Val Asp Val Ile Ile Ser Asp Val Asn Met Pro Asp Lys Thr Gly Leu
         50                  55                  60

Asp Met Ile Arg Glu Met Lys Glu Ile Leu Pro Asp Ala Ala Tyr Ile
 65                  70                  75                  80

Leu Leu Ser Gly Tyr Gln Glu Phe Asp Tyr Val Lys Arg Ala Met Asn
                 85                  90                  95

Leu Ser Val Val Asp Tyr Leu Val Lys Pro Val Asp Lys Val Glu Leu
            100                 105                 110

Gly Asn Leu Leu Glu Lys Ile Ala Gly Gln Leu Gly Glu Arg Gly Lys
        115                 120                 125

Lys Ser Gln Thr Leu Ser Gln Glu Leu Asp Glu Ala Gly Phe Val Ser
    130                 135                 140

Tyr Leu Gly Asp Lys Glu Asn Trp Trp Ile Gly Leu Ser Lys Glu Lys
145                 150                 155                 160

Gln Gly Ser Phe Thr Ile Pro Tyr Tyr Val Leu Gly Gln Ala Trp Gln
                165                 170                 175
```

```
Ile Phe Ile Ser Asp Gln Pro Leu Asp Gly Leu Val Val Thr Pro Phe
            180                 185                 190
Glu Ala Pro Tyr Gln Glu His Phe Glu Arg Trp Lys Leu Asn Ala Glu
            195                 200                 205
Lys Thr Leu Phe Tyr Gly Ser Val Asn Leu Gln Gln Ser Glu Ser Leu
            210                 215                 220
Phe Ala Tyr Tyr Glu Pro Ile Tyr Arg Val Ile Gln Gly Asn Leu
225                 230                 235                 240
Asn Gln Ile Val Glu Glu Leu Asn Leu Leu Glu Lys Val Val Leu Glu
            245                 250                 255
Asn Thr Pro Arg Ile Pro Ile Thr Lys Gln Leu Phe Ile Gln Phe Val
            260                 265                 270
Met Asp Val Phe His Leu Phe Glu His Leu Lys Ala Asp Asp Met Thr
            275                 280                 285
Asp Ile Val Lys Thr Ile His Ala Ile Gln Ser Phe Asp Glu Leu Val
            290                 295                 300
Ser Tyr Ile Lys Glu Thr Leu Ile Ser Phe Phe Gly Gln Tyr Arg Met
305                 310                 315                 320
Asn Glu Asn Val Val Ser Val Leu Glu Val Ile Gly Arg Asp Tyr Gln
            325                 330                 335
Lys Glu Leu Ser Leu Lys Asp Ile Ser Lys Ala Leu Phe Ile Asn Pro
            340                 345                 350
Val Tyr Leu Gly Gln Leu Ile Lys Arg Glu Thr Asp Ser Thr Phe Ala
            355                 360                 365
Glu Leu Leu Asn Lys Gln Arg Ile Lys Ala Ala Gln Gln Leu Leu Leu
            370                 375                 380
Ser Thr Ser Asp Ser Ile Glu Asn Ile Cys Tyr Ala Val Gly Tyr Ser
385                 390                 395                 400
Asn Leu Gly Tyr Phe Tyr Lys Val Phe Arg Lys Leu Cys Gly Lys Ser
            405                 410                 415
Pro Lys Ala Tyr Arg Lys Gln Val Glu Thr Ile Leu
            420                 425
```

<210> SEQ ID NO 5
<211> LENGTH: 3453
<212> TYPE: DNA
<213> ORGANISM: Streptococcus pneumoniae
<220> FEATURE:
<221> NAME/KEY: CDS
<222> LOCATION: (450)...(2129)

<400> SEQUENCE: 5

| | | |
|---|---|---|
| cttatatgca gaacatggtt atagctttcg ggaatacagt ttgaaggagg cttggtctct | 60 |
| ttacaagcaa aattttatct caagcaacct gattttctat agcttttttag gtgtgggtct | 120 |
| agttttgacc tatggtttgt atctcttggt gcaattgcct catcagacca ttgttcattt | 180 |
| gattgcgacc ttttgaatg tcctagtagt tgccctgatc ttttttggctt atacagtatc | 240 |
| tttaaaatta caagtttatt ttgccttgtc ctatcgaaat agtctcaaat tatccttgat | 300 |
| tggcatcttt atgagtctag cagctgtggc taaggttctc cttgggactg tgctacttgt | 360 |
| agcaattggt tactatatgc ctgccctgct attttttgta ggaattggga tgtggcattt | 420 |
| ctttatcagt gatatgttgg aacctgtct atg aaa tca tcc atg aaa aat tgg | 473 |
|                                                    Met Lys Ser Ser Met Lys Asn Trp | |
|                                                     1                  5 | |
| cga caa aat aga atg aag cac ttt tgg cta cat acg ctt cta aga acc | 521 |

```
Arg Gln Asn Arg Met Lys His Phe Trp Leu His Thr Leu Leu Arg Thr
     10              15                  20 tat agt tca gtg atg atc att atc att gcg agt ttt gca atc tta ctc         569
Tyr Ser Ser Val Met Ile Ile Ile Ile Ala Ser Phe Ala Ile Leu Leu
 25              30                  35                  40 tct tac gct gac tgg gat tca cgt gaa aag gaa gcc cag aga gta gcc         617
Ser Tyr Ala Asp Trp Asp Ser Arg Glu Lys Glu Ala Gln Arg Val Ala
                 45                  50                  55 cag cgt gta act gct aga aca gtg agt gaa att gaa tat tac cat aga         665
Gln Arg Val Thr Ala Arg Thr Val Ser Glu Ile Glu Tyr Tyr His Arg
             60                  65                  70 gag tca acc cag ata gct cag gct tta gtt gaa aac caa gct cgt att         713
Glu Ser Thr Gln Ile Ala Gln Ala Leu Val Glu Asn Gln Ala Arg Ile
         75                  80                  85 gag gga atc tat aaa tac ttt agc ctt agc atg cca gac tat ttt tac         761
Glu Gly Ile Tyr Lys Tyr Phe Ser Leu Ser Met Pro Asp Tyr Phe Tyr
     90                  95                 100 tgg caa tta gag cgg aaa gct tcg cct tat ata tca gtc tct ctg tat         809
Trp Gln Leu Glu Arg Lys Ala Ser Pro Tyr Ile Ser Val Ser Leu Tyr
105             110                 115                 120 gaa aat gtt gat gac ctc tat gtt cga aat gat ttt gta act ggg gtg         857
Glu Asn Val Asp Asp Leu Tyr Val Arg Asn Asp Phe Val Thr Gly Val
                125                 130                 135 gcc att gct ttt caa gat tac aag gaa gtc tat gtt tct act aaa gac         905
Ala Ile Ala Phe Gln Asp Tyr Lys Glu Val Tyr Val Ser Thr Lys Asp
            140                 145                 150 aaa cgt agt gga gaa aaa atc agg gct gag gat ttc aaa cca gca gga         953
Lys Arg Ser Gly Glu Lys Ile Arg Ala Glu Asp Phe Lys Pro Ala Gly
        155                 160                 165 aat agt ttt gcc att cca gtg tca gat cca gtg tca gat caa gac tta        1001
Asn Ser Phe Ala Ile Pro Val Ser Asp Pro Val Ser Asp Gln Asp Leu
170                 175                 180 gga gtg att tac atc tcc ttg gat cct gct gtt tta tac cat gcc att        1049
Gly Val Ile Tyr Ile Ser Leu Asp Pro Ala Val Leu Tyr His Ala Ile
185                 190                 195                 200 gat aat act aga ggt cat act ccg atg gca gta aca gtg acc gaa cct        1097
Asp Asn Thr Arg Gly His Thr Pro Met Ala Val Thr Val Thr Glu Pro
                205                 210                 215 ttt gat acg gag att ttt cat att ggt gag aca gtt gat aag gag agt        1145
Phe Asp Thr Glu Ile Phe His Ile Gly Glu Thr Val Asp Lys Glu Ser
            220                 225                 230 gaa aat tgg cta gtt ggc tta act tct cat ggt tat cag gtt cag gtg        1193
Glu Asn Trp Leu Val Gly Leu Thr Ser His Gly Tyr Gln Val Gln Val
        235                 240                 245 gca gtt ccc aaa aac ttt gtt tta caa gga acg gtg acc agc tct gct        1241
Ala Val Pro Lys Asn Phe Val Leu Gln Gly Thr Val Thr Ser Ser Ala
250                 255                 260 ttg att gtg ggc ttg agc ctt ctc ttt att gtc att ctt tat ctg act        1289
Leu Ile Val Gly Leu Ser Leu Leu Phe Ile Val Ile Leu Tyr Leu Thr
265                 270                 275                 280 ttg agg cag acc ttt gct aat tat caa aag cag gta gtg gat ttg gtg        1337
Leu Arg Gln Thr Phe Ala Asn Tyr Gln Lys Gln Val Val Asp Leu Val
                285                 290                 295 gat tcc atc caa gct att gcc caa gga caa gaa ggt ctt cgc att gat        1385
Asp Ser Ile Gln Ala Ile Ala Gln Gly Gln Glu Gly Leu Arg Ile Asp
            300                 305                 310 acg ctt gaa aag gat cag gaa ttg ctc cta atc gcg gag acg acc aat        1433
Thr Leu Glu Lys Asp Gln Glu Leu Leu Leu Ile Ala Glu Thr Thr Asn
        315                 320                 325
```

-continued

```
gat atg ttg gat cga ttg gaa aag aat atc cat gat att tac cag tta    1481
Asp Met Leu Asp Arg Leu Glu Lys Asn Ile His Asp Ile Tyr Gln Leu
    330                 335                 340 gaa ctc agt caa aaa gat gcc aat atg cgg gcc ttg cag gcg caa atc    1529
Glu Leu Ser Gln Lys Asp Ala Asn Met Arg Ala Leu Gln Ala Gln Ile
345                 350                 355                 360 aat cct cat ttt atg tat aat acg ctg gag ttc ttg cgc atg tat gca    1577
Asn Pro His Phe Met Tyr Asn Thr Leu Glu Phe Leu Arg Met Tyr Ala
                365                 370                 375 gtt atg cag agt caa gat gag ttg gca gat atc att tat gaa ttc agt    1625
Val Met Gln Ser Gln Asp Glu Leu Ala Asp Ile Ile Tyr Glu Phe Ser
            380                 385                 390 agt ctc ttg cgt aac aat att tcc gac gaa aga gag acc ctc ctc aaa    1673
Ser Leu Leu Arg Asn Asn Ile Ser Asp Glu Arg Glu Thr Leu Leu Lys
        395                 400                 405 cag gaa tta gaa ttt tgc cgt aaa tac agc tat ctc tgc atg gtt cgc    1721
Gln Glu Leu Glu Phe Cys Arg Lys Tyr Ser Tyr Leu Cys Met Val Arg
    410                 415                 420 tat ccc aag tcc att gcc tat ggt ttc aag ata gat cca gag tta gag    1769
Tyr Pro Lys Ser Ile Ala Tyr Gly Phe Lys Ile Asp Pro Glu Leu Glu
425                 430                 435                 440 aat atg aag att ccc aag ttt acc ttg caa ccg ctg gta gaa aac tat    1817
Asn Met Lys Ile Pro Lys Phe Thr Leu Gln Pro Leu Val Glu Asn Tyr
                445                 450                 455 ttc gcg cat ggt gtt gac cac agg cgg aca gat aat gtg att agc atc    1865
Phe Ala His Gly Val Asp His Arg Arg Thr Asp Asn Val Ile Ser Ile
            460                 465                 470 aag gct ctt aaa cag gat ggt ttt gtg gaa att ttg gtg gtc gat aat    1913
Lys Ala Leu Lys Gln Asp Gly Phe Val Glu Ile Leu Val Val Asp Asn
        475                 480                 485 ggt aga gga atg tcg gct gaa aag ttg gca aat atc cga gaa aaa tta    1961
Gly Arg Gly Met Ser Ala Glu Lys Leu Ala Asn Ile Arg Glu Lys Leu
    490                 495                 500 agt cag aga tat ttt gaa cac caa gcc agc tac agt gat caa agg cag    2009
Ser Gln Arg Tyr Phe Glu His Gln Ala Ser Tyr Ser Asp Gln Arg Gln
505                 510                 515                 520 tct atc ggg att gtc aat gta cac gag cgt ttt gtg ctc tat ttt gga    2057
Ser Ile Gly Ile Val Asn Val His Glu Arg Phe Val Leu Tyr Phe Gly
                525                 530                 535 gac cgc tat gcc att act ata gag tct gca gag caa gcc ggt gtt cag    2105
Asp Arg Tyr Ala Ile Thr Ile Glu Ser Ala Glu Gln Ala Gly Val Gln
            540                 545                 550 tat cgt att aca att caa gat gag tagaaaggga gaaaatgtat aaagtattat   2159
Tyr Arg Ile Thr Ile Gln Asp Glu
        555                 560 tagtagatga tgagtacatg gtgacagaag gtctgaagcg tttgattccc tttgataagt  2219
gggatatgga ggtcgtcgca acagtcagtc atgccgatga agctctagaa tatgttcagg  2279
aaaatcctgt cgatgtcatc atttccgatg tcaatatgcc agacaaaaca gggcttgata  2339
tgattcggga gatgaaagag atcttaccag atgctgccta tcctgctc tcaggttatc    2399 aggagtttga ttatgtaaaa agagcaatga atcttagtgt ggtggactat ttggtcaaac  2459
ctgttgataa ggtagagctg ggaaatctgc tggagaagat tgcaggtcag ctcggcgaga  2519
gagggaagaa aagtcagact cttagtcaag aattagcga ggctggattt gttagttatt   2579
taggggataa ggagaattgg tggataggtc tatccaagga aaaacaaggt tccttcacca  2639
ttccctacta tgtcttggga caagcctggc agattttcat ttctgaccaa ccctagatg   2699 gtttagtcgt tacacctttt gaagctcctt atcaagaaca ttttgaacgc tggaagctga  2759
```

-continued

```
atgctgagaa aaccctctttt tacggttctg taaatctgca gcagtctgag agtctctttg    2819
cctattacga accgatttat agggttatca ttcagggaaa tctcaatcaa atcgtagaag    2879
agttaaatct cttggagaag gtagttcttg aaaatacgcc gcgaattccg attactaaac    2939 agcttttttat ccagtttgtc atggatgtct tccatttatt tgaacatctc aaagctgatg    2999
atatgacgga cattgtcaaa accattcatg ctattcaatc cttcgatgaa ttggtttctt    3059
atatcaagga aactctgatc agcttttttcg gtcaataccg tatgaatgaa aatgtggtca    3119
gtgtgctgga agtcattggt cgtgattacc aaaaagagct ttccctcaag gatatcagta    3179
aggccctctt tatcaatcct gtctatctag ggcagttgat taagcgtgaa accgattcga    3239
cctttgcaga gttactaaac aaacaacgta ttaaggctgc ccaacaactt ttgctttcaa    3299
ctagtgacag catcgaaaat atttgttatg ctgttggtta cagtaacctt ggatatttct    3359 ataaagttttt ccgaaaattg tgcggaaaat cgccaaaagc ctaccgaaaa caggtagaaa    3419
ctatactata agatttgtat tcctttacaa aatg    3453
```

<210> SEQ ID NO 6
<211> LENGTH: 560
<212> TYPE: PRT
<213> ORGANISM: Streptococcus pneumoniae

<400> SEQUENCE: 6

```
Met Lys Ser Ser Met Lys Asn Trp Arg Gln Asn Arg Met Lys His Phe
 1               5                   10                  15

Trp Leu His Thr Leu Leu Arg Thr Tyr Ser Ser Val Met Ile Ile Ile
            20                  25                  30

Ile Ala Ser Phe Ala Ile Leu Leu Ser Tyr Ala Asp Trp Asp Ser Arg
        35                  40                  45

Glu Lys Glu Ala Gln Arg Val Ala Gln Arg Val Thr Ala Arg Thr Val
    50                  55                  60

Ser Glu Ile Glu Tyr Tyr His Arg Glu Ser Thr Gln Ile Ala Gln Ala
65                  70                  75                  80

Leu Val Glu Asn Gln Ala Arg Ile Glu Gly Ile Tyr Lys Tyr Phe Ser
                85                  90                  95

Leu Ser Met Pro Asp Tyr Phe Tyr Trp Gln Leu Glu Arg Lys Ala Ser
            100                 105                 110

Pro Tyr Ile Ser Val Ser Leu Tyr Glu Asn Val Asp Asp Leu Tyr Val
        115                 120                 125

Arg Asn Asp Phe Val Thr Gly Val Ala Ile Ala Phe Gln Asp Tyr Lys
    130                 135                 140

Glu Val Tyr Val Ser Thr Lys Asp Lys Arg Ser Gly Glu Lys Ile Arg
145                 150                 155                 160

Ala Glu Asp Phe Lys Pro Ala Gly Asn Ser Phe Ala Ile Pro Val Ser
                165                 170                 175

Asp Pro Val Ser Asp Gln Asp Leu Gly Val Ile Tyr Ile Ser Leu Asp
            180                 185                 190

Pro Ala Val Leu Tyr His Ala Ile Asp Asn Thr Arg Gly His Thr Pro
        195                 200                 205

Met Ala Val Thr Val Thr Glu Pro Phe Asp Thr Glu Ile Phe His Ile
    210                 215                 220

Gly Glu Thr Val Asp Lys Glu Ser Glu Asn Trp Leu Val Gly Leu Thr
225                 230                 235                 240

Ser His Gly Tyr Gln Val Gln Val Ala Val Pro Lys Asn Phe Val Leu
```

```
                        245                 250                 255
        Gln Gly Thr Val Thr Ser Ser Ala Leu Ile Val Gly Leu Ser Leu Leu
                        260                 265                 270
        Phe Ile Val Ile Leu Tyr Leu Thr Leu Arg Gln Thr Phe Ala Asn Tyr
                    275                 280                 285
        Gln Lys Gln Val Val Asp Leu Val Asp Ser Ile Gln Ala Ile Ala Gln
                    290                 295                 300
        Gly Gln Glu Gly Leu Arg Ile Asp Thr Leu Glu Lys Asp Gln Glu Leu
        305                 310                 315                 320
        Leu Leu Ile Ala Glu Thr Thr Asn Asp Met Leu Asp Arg Leu Glu Lys
                        325                 330                 335
        Asn Ile His Asp Ile Tyr Gln Leu Glu Leu Ser Gln Lys Asp Ala Asn
                        340                 345                 350
        Met Arg Ala Leu Gln Ala Gln Ile Asn Pro His Phe Met Tyr Asn Thr
                    355                 360                 365
        Leu Glu Phe Leu Arg Met Tyr Ala Val Met Gln Ser Gln Asp Glu Leu
                    370                 375                 380
        Ala Asp Ile Ile Tyr Glu Phe Ser Ser Leu Leu Arg Asn Asn Ile Ser
        385                 390                 395                 400
        Asp Glu Arg Glu Thr Leu Leu Lys Gln Glu Leu Glu Phe Cys Arg Lys
                        405                 410                 415
        Tyr Ser Tyr Leu Cys Met Val Arg Tyr Pro Lys Ser Ile Ala Tyr Gly
                        420                 425                 430
        Phe Lys Ile Asp Pro Glu Leu Glu Asn Met Lys Ile Pro Lys Phe Thr
                    435                 440                 445
        Leu Gln Pro Leu Val Glu Asn Tyr Phe Ala His Gly Val Asp His Arg
                    450                 455                 460
        Arg Thr Asp Asn Val Ile Ser Ile Lys Ala Leu Lys Gln Asp Gly Phe
        465                 470                 475                 480
        Val Glu Ile Leu Val Val Asp Asn Gly Arg Gly Met Ser Ala Glu Lys
                        485                 490                 495
        Leu Ala Asn Ile Arg Glu Lys Leu Ser Gln Arg Tyr Phe Glu His Gln
                        500                 505                 510
        Ala Ser Tyr Ser Asp Gln Arg Gln Ser Ile Gly Ile Val Asn Val His
                    515                 520                 525
        Glu Arg Phe Val Leu Tyr Phe Gly Asp Arg Tyr Ala Ile Thr Ile Glu
                    530                 535                 540
        Ser Ala Glu Gln Ala Gly Val Gln Tyr Arg Ile Thr Ile Gln Asp Glu
        545                 550                 555                 560

<210> SEQ ID NO 7
<211> LENGTH: 25
<212> TYPE: DNA
<213> ORGANISM: Streptococcus pneumoniae

<400> SEQUENCE: 7
atgtataaag tattattagt agatg                                          25

<210> SEQ ID NO 8
<211> LENGTH: 25
<212> TYPE: DNA
<213> ORGANISM: Streptococcus pneumoniae

<400> SEQUENCE: 8
tagtatagtt tctacctgtt ttcgg                                          25
```

```
<210> SEQ ID NO 9
<211> LENGTH: 25
<212> TYPE: DNA
<213> ORGANISM: Streptococcus pneumoniae

<400> SEQUENCE: 9
aactgagact ggctttaaga gatta                                              25
```

RESPONSE REGULATOR

RELATED APPLICATIONS

This application is a divisional of U.S. application Ser. No. 09/139,064, filed Aug. 25, 1998.

This application claims benefit of U.S. Provisional Patent Application No. 60/060,714, filed Sep. 9, 1997.

FIELD OF THE INVENTION

This invention relates to newly identified polynucleotides and polypeptides, and their production and uses, as well as their variants, agonists and antagonists, and their uses. In particular, the invention relates to polynucleotides and polypeptides of the response regulator family, as well as their variants, hereinafter referred to as "Response regulator," "Response regulator polynucleotide(s)," and "Response regulator polypeptide(s)" as the case may be.

BACKGROUND OF THE INVENTION

The Streptococci make up a medically important genera of microbes known to cause several types of disease in humans, including, for example, otitis media, conjunctivitis, pneumonia, bacteremia, meningitis, sinusitis, pleural empyema and endocarditis, and most particularly meningitis, such as for example infection of cerebrospinal fluid. Since its solution more than 100 years ago, Streptococcus pneumoniae has been one of the more intensively studies microbes. For example, much of our early understanding that DNA is, in fact, the genetic material was predicted on the work of Griffith and of Avery, Macleod and McCarty using this microbe. Despite the vast amount of research with Streptococcus pneumoniae, many questions concerning the virulence of this microbe remain. It is particularly preferred to employ Streptococcal genes and gene products as targets for the development of antibiotics.

While certain Streptococcal factors associated with pathogenicity have been identified, e.g., capsule polysaccharides, pepidoglycans, pneumolysins, PspA Complement factor H binding component, autolysin, neuraminidase, peptide permeases, hydrogen peroxide, IgA1 protease, the list is certainly not complete. Further very little is known concerning the temporal expression of such genes during infection and disease progression in a mammalian host. Discovering the sets of genes the bacteriumis like to be expressing at the different stages of infection, particularly when an infection is established, provides critical information for the screening and characterization of novel antibacterials which can interrupt pathogenesis. In addition to providing a fuller understanding of known proteins, such an approach will identify previously unrecognised targets.

Many two component signal transduction systems (TCSTS) have been identified in bacteria (Stock, J. B., Ninfa, A. J. & Stock, A. M. (1989) Microbiol Rev. 53, 450–490). There are involved in the bacterium's ability to monitor its surroundings and adapt to changes in its environment. Several of these bacterial TCSTS are involved in virulence and bacterial pathogenesis within the host.

Response regulators are components of the TCSTS. These proteins are phosphorylated by histidine kinases and in turn once phosphorylated effect the response, often through a DNA binding domain becoming activated. The response regulators are characterized by a conserved N-terminal domain of approximately 100 amino acids. The N-terminal domains of response regulators as well as retaining five functionally important residues, corresponding to the residues D12, D13, D57, D87, K109 in CheY (Matsumura, P., Rydel, J. J., Linzmeier, R. & Vacante, D. (1984) J. Bacteriol. 160, 36–41), have conserved structural features (Volz, K. (1993) Biochemistry 32, 11741–11753). The 3-dimensional structures of CheY from *Salmonella typhimurium* (Stock, A. M., Mottonen, J. M., Stock, J. B. & Schutt, C. E. (1989) Nature, 337, 745–749) and *Escherichia coli* (Volz, K. & Matsumura, P. (1991) J. Biol. Chem. 266, 15511–15519) and the N-terminal domain of nitrogen regulatory protein C from *S.typhimurium* (Volkman, B. F., Nohaile, M. J., Amy, N. K., Kustu, S. & Wemmer, D. E. (1995) Biochemistry, 34 1413–1424), are available, as well as the secondary structure of SpoOF from *Bacillus subtilis* (Feher, V. A., Zapf, J. W., Hoch, J. A., Dahlquist, F. W., Whiteley, J. M. & Cavanagh, J. (1995) Protein Science, 4, 1801–1814). These structures have a ($\alpha/\beta$)5 fold. Several structural residues are conserved between different response regulator sequences, specifically hydrophobic residues within the β-sheet hydrophobic core and sites from the α-helices. This family of response regulators includes DegU protein from *Bacillus subtilis*. DegU is the response regulator of the TCSTS involved in regulating the production of extracellular proteases (Henner, D. J., Yang, M. & Ferrari, E. (1988) J. Bacteriol. 170, 5102–5109).

Histidine kinases are components of the TCSTS which autophosphorylate a histidine residue. The phosphate group is then transferred to the cognate response regulator. The Histidine kinases have five short conserved amino acid sequences (Stock, J. B., Ninfa, A. J. & Stock, A. M. (1989) Microbiol. Rev. 53, 450–490, Swanson, R. V., Alex, L. A. & Simon, M. I. (1994) TIBS 19 485–491). These are the histidine residue, which is phosphorylated, followed after approximately 100 residues by a conserved asparagine residue. After another 15 to 45 residues a DXGXG motif is found, followed by a FXXF motif after another 10–20 residues. 10–20 residues further on another glycine motif, GXG is found. The two glycine motifs are thought to be involved in nucleotide binding.

Among the processes regulated by TCSTS are production of virulence factors, motility, antibiotic resistance and cell replication. Inhibitors of TCSTS proteins would prevent the bacterium from establishing and maintaining infection of the host by preventing it from producing the necessary factors for pathogenesis and thereby have utility in anti-bacterial therapy.

The frequency of Streptococcus pneumoniae infections has risen dramatically in the past few decades. This has been attributed to the emergence of multiple antibiotic resistant strains and an increasing population of people with weakened immune systems. It is no longer uncommon to isolate Streptococcus pneumoniae strains which are resistant to some or all of the standard antibiotics. This phenomenon has created an unmet medical need and demand for new antimicrobial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides and polypeptides, such as the Response regulator embodiments of the invention, that have a present benefit of, among other things, being useful to screen compounds for antimicrobial activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

SUMMARY OF THE INVENTION

The present invention relates to Response regulator, in particular Response regulator polypepties and Response regulator polynucleotides, recombinant materials and methods for their production. In another aspect, the invention relates to methods for using such polypeptides and polynucleotides, including treatment of microbial diseases, amongst others. In a further aspect, the invention relates to methods for identifying agonists and antagonists using the materials provided by the invention, and for treating microbial infections and conditions associated with such infections with the identified agonist or antagonist compounds. In a still further aspect, the invention relates to diagnostic assays for detecting diseases associated with microbial infections and conditions associated with such infections, such as assays for detecting Response regulator expression or activity.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to Response regulator polypeptides and polynucleotides as described in greater detail below. In particular, the invention relates to polypeptides and polynucleotides of a Response regulator of Streptococcus pneumoniae, which is related by amino acid sequence homology to DegU from *Bacillus subtilis* polypeptide. The invention relates especially to Response regulator having the nucleotide and amino acid sequences set out in Table 1 as SEQ ID NO:1 or 3 and SEQ ID NO:2 or 4 respectively. Note that sequences recited in the Sequence Listing below as "DNA" represent an exemplification of the invention, since those of ordinary skill will recognize that such sequences can be usefully employed in polynucleotides in general, including ribopolynucleotides.

TABLE 1

Response regulator Polynucleotide and Polypeptide Sequences (A) *Streptococcus pneumoniae* Response regulator polynucleotide sequence
[SEQ ID NO: 1].
5'-
CTTATATGCAGAACATGGTTATAGCTTTCGGGAATACAGTTTGAAGGAGGCTTGGTCTCTTTACAAGCAAAA

TTTTATCTCAAGCAACCTGATTTTCTATAGCTTTTTAGGTGTGGGTCTAGTTTTGACCTATGGTTTGTATCT

CTTGGTGCAATTGCCTCATCAGACCATTGTTCATTTGATTGCGACCCTTTTGAATGTCCTAGTAGTTGCCCT

GATCTTTTTGGCTTATACAGTATCTTTAAAATTACAAGTTTATTTTGCCTTGTCCTATCGAAATAGTCTCAA

ATTATCCTTGATTGGCATCTTTATGAGTCTAGCAGCTGTGGCTAAGGTTCTCCTTGGGACTGTGCTACTTGT

AGCAATTGGTTACTATATGCCTGCCCTGCTATTTTTTGTAGGAATTGGGATGTGGCATTTCTTTATCAGTGA

TATGTTGGAACCTGTCTATGAAATCATCCATGAAAAATTGGCGACAAAATAGAATGAAGCACTTTTGGCTAC

ATACGCTTCTAAGAACCTATAGTTCAGTGATGATCATTATCATTGCGAGTTTTGCAATCTTACTCTCTTACG

CTGACTGGGATTCACGTGAAAAGGAAGCCCAGAGAGTAGCCCAGCGTGTAACTGCTAGAACAGTGAGTGAAA

TTGAATATTACCATAGAGAGTCAACCCAGATAGCTCAGGCTTTAGTTGAAAACCAAGCTCGTATTGAGGGAA

TCTATAAATACTTTAGCCTTAGCATGCCAGACTATTTTTACTGGCAATTAGAGCGGAAAGCTTCGCCTTATA

TATCAGTCTCTCTGTATGAAAATGTTGATGACCTCTATGTTCGAAATGATTTTGTAACTGGGGTGGCCATTG

CTTTTCAAGATTACAAGGAAGTCTATGTTTCTACTAAAGACAAACGTAGTGGAGAAAAAATCAGGGCTGAGG

ATTTCAAACCAGCAGGAAATAGTTTTGCCATTCCAGTGTCAGATCCAGTGTCAGATCAAGACTTAGGAGTGA

TTTACATCTCCTTGGATCCTGCTGTTTTATACCATGCCATTGATAATACTAGAGGTCATACTCCGATGGCAG

TAACAGTGACCGAACCTTTTGATACGGAGATTTTTCATATTGGTGAGACAGTTGATAAGGAGAGTGAAAATT

GGCTAGTTGGCTTAACTTCTCATGGTTATCAGGTTCAGGTGGCAGTTCCCAAAAACTTTGTTTTACAAGGAA

CGGTGACCAGCTCTGCTTTGATTGTGGGCTTGAGCCTTCTCTTTATTGTCATTCTTTATCTGACTTTGAGGC

AGACCTTTGCTAATTATCAAAAGCAGGTAGTGGATTTGGTGGATTCCATCCAAGCTATTGCCCAAGGACAAG

AAGGTCTTCGCATTGATACGCTTGAAAAGGATCAGGAATTGCTCCTAATCGCGGAGACGACCAATGATATGT

TGGATCGATTGGAAAAGAATATCCATGATATTTACCAGTTAGAACTCAGTCAAAAAGATGCCAATATGCGGG

TABLE 1-continued

Response regulator Polynucleotide and Polypeptide Sequences

```
CCTTGCAGGCGCAAATCAATCCTCATTTTATGTATAATACGCTGGAGTTCTTGCGCATGTATGCAGTTATGC

AGAGTCAAGATGAGTTGGCAGATATCATTTATGAATTCAGTAGTCTCTTGCGTAACAATATTTCCGACGAAA

GAGAGACCCTCCTCAAACAGGAATTAGAATTTTGCCGTAAATACAGCTATCTCTGCATGGTTCGCTATCCCA

AGTCCATTGCCTATGGTTTCAAGATAGATCCAGAGTTAGAGAATATGAAGATTCCCAAGTTTACCTTGCAAC

CGCTGGTAGAAAACTATTTCGCGCATGGTGTTGACCACAGGCGGACAGATAATGTGATTAGCATCAAGGCTC

TTAAACAGGATGGTTTTGTGGAAATTTTGGTGGTCGATAATGGTAGAGGAATGTCGGCTGAAAAGTTGGCAA

ATATCCGAGAAAAATTAAGTCAGAGATATTTTGAACACCAAGCCAGCTACAGTGATCAAAGGCAGTCTATCG

GGATTGTCAATGTACACGAGCGTTTTGTGCTCTATTTTGGAGACCGTATGCCATTACTATAGAGTCTGCAG

AGCAAGCCGGTGTTCAGTATCGTATTACAATTCAAGATGAGTAGAAAGGGAGAAAATGTATAAAGTATTATT

AGTAGATGATGAGTACATGGTGACAGAAGGTCTGAAGCGTTTGATTCCCTTTGATAAGTGGGATATGGAGGT

CGTCGCAACAGTCAGTCATGCCGATGAAGCTCTAGAATATGTTCAGGAAAATCCTGTCGATGTCATCATTTC

CGATGTCAATATGCCAGACAAAACAGGGCTTGATATGATTCGGGAGATGAAAGAGATCTTACCAGATGCTGC

CTATATCCTGCTCTCAGGTTATCAGGAGTTTGATTATGTAAAAAGAGCAATGAATCTTAGTGTGGTGGACTA

TTTGGTCAAACCTGTTGATAAGGTAGAGCTGGGAAATCTGCTGGAGAAGATTGCAGGTCAGCTCGGCGAGAG

AGGGAAGAAAAGTCAGACTCTTAGTCAAGAATTAGACGAGGCTGGATTTGTTAGTTATTTAGGGGATAAGGA

GAATTGGTGGATAGGTCTATCCAAGGAAAAACAAGGTTCCTTCACCATTCCCTACTATGTCTTGGGTCAAGC

CTGGCAGATTTTCATTTCTGACCAACCCCTAGATGGTTTAGTCGTTACACCTTTTGAAGCTCCTTATCAAGA

ACATTTTGAACGCTGGAAGCTGAATGCTGAGAAAACCCTCTTTTACGGTTCTGTAAATCTGCAGCAGTCTGA

GAGTCTCTTTGCCTATTACGAACCGATTTATAGGGTTATCATTCAGGGAAATCTCAATCAAATCGTAGAAGA

GTTAAATCTCTTGGAGAAGGTAGTTCTTGAAAATACGCCGCGAATTCCGATTACTAAACAGCTTTTTATCCA

GTTTGTCATGGATGTCTTCCATTTATTTGAACATCTCAAAGCTGATGATATGACGGACATTGTCAAAACCAT

TCATGCTATTCAATCCTTCGATGAATTGGTTTCTTATATCAAGGAAACTCTGATCAGCTTTTTCGGTCAATA

CCGTATGAATGAAAATGTGGTCAGTGTGCTGGAAGTCATTGGTCGTGATTACCAAAAAGAGCTTTCCCTCAA

GGATATCAGTAAGGCCCTCTTTATCAATCCTGTCTATCTAGGGCAGTTGATTAAGCGTGAAACCGATTCGAC

CTTTGCAGAGTTACTAAACAAACAACGTATTAAGGCTGCCCAACAACTTTTGCTTTCAACTAGTGACAGCAT

CGAAAATATTTGTTATGCTGTTGGTTACAGTAACCTTGGATATTTCTATAAAGTTTTCCGAAAATTGTGCGG

AAAATCGCCAAAAGCCTACCGAAAACAGGTAGAAACTATACTATAAGATTTGTATTCCTTTACAAAATG
-3'
```

(B) *Streptococcus pneumoniae* Response regulator polypeptide
sequence deduced from a polynucleotide sequence in this table
[SEQ ID NO:2].
NH$_2$-

MYKVLLVDDEYMVTEGLKRLIPFDKWDMEVVATVSHADEALEYVQENPVDVIISDVNMPDKTGLDMIREMKE

ILPDAAYILLSGYQEFDYVKRAMNLSVVDYLVKPVDKVELGNLLEKIAGQLGERGKKSQTLSQELDEAGFVS

YLGDKENWWIGLSKEKQGSFTIPYYVLGQAWQIFISDQPLDGLVVTPFEAPYQEHFERWKLNAEKTLFYGSV

NLQQSESLFAYYEPIYRVIIQGNLNQIVEELNLLEKVVLENTPRIPITKQLFIQFVMDVFHLFEHLKADDMT

DIVKTIHAIQSFDELVSYIKETLISFFGQYRMNENVVSVLEVIGRDYQKELSLKDISKALFINPVYLGQLIK

RETDSTFAELLNKQRIKAAQQLLLSTSDSIENICYAVGYSNLGYFYKVFRKLCGKSPKAYRKQVETIL

-COOH (C) *Streptococcus pneumoniae* Response regulator ORF sequence
[SEQ ID NO:3].
5'-
CTTATATGCAGAACATGGTTATAGCTTTCGGGAATACAGTTTGAAGGAGGCTTGGTCTCTTTACAAGCAAAA TABLE 1-continued Response regulator Polynucleotide and Polypeptide Sequences TTTTATCTCAAGCAACCTGATTTTCTATAGCTTTTTAGGTGTGGGTCTAGTTTTGACCTATGGTTTGTATCT
CTTGGTGCAATTGCCTCATCAGACCATTGTTCTTTGATTGCGACCCTTTTGAATGTCCTAGTAGTTGCCCCT
GATCTTTTTGGCTTATACAGTATCTTTAAAATTACAAGTTTATTTTGCCTTGTCCTATCAAAATAGTCTCAA
ATTATCCTTGATTGGCATCTTTATGAGTCTAGCAGCTGTGGCTAAGGTTCTCCTTGGGACTGTGCTACTTGT
AGCAATTGGTTACTATATGCCTGCCCTGCTATTTTTTGTAGGAATTGGGATGTGGCATTTCTTTATCAGTGA
TATGTTGGAACCTGTCTATGAAATCATCCATGAAAAATTGGCGACAAAATAGAATGAAGCACTTTTGGCTAC
ATACGCTTCTAAGAACCTATAGTTCAGTGATGATCATTATCATTGCGAGTTTTGCAATCTTACTCTCTTACG
CTGACTGGGATTCACGTGAAAAGGAAGCCCAGAGAGTAGCCCAGCGTGTAACTGCTAGAACAGTGAGTGAAA
TTGAATATTACCATAGAGAGTCAACCCAGATAGCTCAGGCTTTAGTTGAAAACCAAGCTCGTATTGAGGGAA
TCTATAAATACTTTAGCCTTAGCATGCCAGACTATTTTTACTGGCAATTAGAGCGGAAAGCTTCGCCTTATA
TATCAGTCTCTCTGTATGAAAATGTTGATGACCTCTATGTTCGAAATGATTTTGTAACTGGGGTGGCCATTG
CTTTTCAAGATTACAAGGAAGTCTATGTTTCTACTAAAGACAAACGTAGTGGAGAAAAAATCAGGGCTGAGG
ATTTCAAACCAGCAGGAAATAGTTTTGCCATTCCAGTGTCAGATCCAGTGTCAGATCAAGACTTAGGAGTGA
TTTACATCTCCTTGGATCCTGCTGTTTTATACCATGCCATTGATAATACTAGAGGTCATACTCCGATGGCAG
TAACAGTGACCGAACCTTTTGATACGGAGATTTTTCATATTGGTGAGACAGTTGATAAGGAGAGTGAAAATT
GGCTAGTTGGCTTAACTTCTCATGGTTATCAGGTTCAGGTGGCAGTTCCCAAAAACTTTGTTTTACAAGGAA
CGGTGACCAGCTCTGCTTTGATTGTGGGCTTGAGCCTTCTCTTTATTGTCATTCTTTATCTGACTTTGAGGC
AGACCTTTGCTAATTATCAAAAGCAGGTAGTGGATTTGGTGGATTCCATCCAAGCTATTGCCCAAGGACAAG
AAGGTCTTCGCATTGATACGCTTGAAAAGGATCAGGAATTGCTCCTAATCGCGGAGACGACCAATGATATGT
TGGATCGATTGGAAAAGAATATCCATGATATTTACCAGTTAGAACTCAGTCAAAAAGATGCCAATATGCGGG
CCTTGCAGGCGCAAATCAATCCTCATTTTATGTATAATACGCTGGAGTTCTTGCGCATGTATGCAGTTATGC
AGAGTCAAGATGAGTTGGCAGATATCATTTATGAATTCAGTAGTCTCTTGCGTAACAATATTTCCGACGAAA
GAGAGACCCTCCTCAAAGAGGAATTAGAATTTTGCCGTAAATACAGCTATCTCTGCATGGTTCGCTATCCCA
AGTCCATTGCCTATGGTTTCAAGATAGATCCAGAGTTAGAGAATATGAAGATTCCCAAGTTTACCTTGCAAC
CGCTGGTAGAAAACTATTTCGCGCATGGTGTTGACCACAGGCGGACAGATAATGTGATTAGCATCAAGGCTC
TTAAACAGGATGGTTTTGTGGAAATTTTGGTGGTCGATAATGGTAGAGGAATGTCGGCTGAAAAGTTGGCAA
ATATCCGAGAAAAATTAAGTCAGAGATATTTTGAACACCAAGCCAGCTACAGTGATCAAAGGCAGTCTATCG
GGATTGTCAATGTACACGAGCGTTTTGTGCTCTATTTTGGAGACCGCTATGCCATTACTATAGAGTCTGCAG
AGCAAGCCGGTGTTCAGTATCGTATTACAATTCAAGATGAGTAGAAAGGGAGAAAATGTATAAAGTATTATT
AGTAGATGATGAGTACATGGTGACAGAAGGTCTGAAGCGTTTGATTCCCTTTGATAAGTGGGATATGGAGGT
CGTCGCAACAGTCAGTCATGCCGATCAAGCTCTAGAATATGTTCAGGAAAATCCTGTCGATGTCATCATTTC
CGATGTGAATATGCCAGACAAAACAGGGCTTGATATGATTCGGGAGATGAAAGAGATCTTACCAGATGCTGC
CTATATCCTGCTCTCAGGTTATCAGGAGTTTGATTATGTAAAAAGAGCAATGAATCTTAGTGTGGTGGACTA
TTTGGTCAAACCTGTTGATAAGGTAGAGCTGGGAAATCTGCTGGAGAAGATTGCAGGTCAGCTCGGCGAGAG
AGGGAAGAAAAGTCAGACTCTTAGTCAAGAATTAGACGAGGCTGGATTTGTTAGTTATTTAGGGGATAAGGA
GAATTGGTGGATAGGTCTATCGAAGGAAAAACAAGGTTCCTTCACCATTCCCTACTATGTCTTGGGTCAAGC
CTGGCAGATTTTCATTTCTGACCAACCCCTAGATGGTTTAGTCGTTACACCTTTTGAAGCTCCTTATCAAGA
ACATTTTGAACGCTGGAAGCTGAATGCTGAGAAAACCCTCTTTTACGGTTCTGTAAATCTGCAGCAGTCTGA TABLE 1-continued Response regulator Polynucleotide and Polypeptide Sequences

GAGTCTCTTTGCCTATTACGAACCGATTTATAGGGTTATCATTCAGGGAAATCTCAATCAAATCGTAGAAGA

GTTAAATCTCTTGGAGAAGGTAGTTCTTGAAAATACGCCGCGAATTCCGATTACTAAACAGCTTTTTATCCA

GTTTGTCATGGATGTCTTCCATTTATTTGAACATCTCAAAGCTGATGATATGACGGACATTGTCAAAACCAT

TCATGCTATTCAATCCTTCGATGAATTGGTTTCTTATATCAAGGAAACTCTGATCAGCTTTTTCGGTCAATA

CCGTATGAATGAAAATGTGGTCAGTGTGCTGGAAGTCATTGGTCGTGATTACCAAAAAGAGCTTTCCCTCAA

GGATATCAGTAAGGCCCTCTTTATCAATCCTGTCTATCTAGGGCAGTTGATTAAGCGTGAAACCGATTCGAC

CTTTGCAGAGTTACTAAACAAACAACGTATTAAGGCTGCCCAACAACTTTTGCTTTCAACTAGTGACAGCAT

CGAAAATATTTGTTATGCTGTTGGTTACAGTAACCTTGGATATTTCTATAAACTTTTCCGAAAATTGTGCGG

AAAATCGCCAAAAGCCTACCGAAAACAGGTAGAAACTATACTATAAGATTTGTATTCCTTTACAAAATG (D) *Streptococcus pneumoniae* Response regulator polypeptide
sequence deduced from a polynucleotide ORF sequence in this table
[SEQ ID NO:4].
NH2-

MYKVLLVDDEYMVTEGLKRLIPFDKWDMEVVATVSHADEALEYVQENPVDVIISDVNMPDKTGLDMIREMKE

ILPDAAYILLSGYQEFDYVKRAMNLSVVDYLVKPVDKVELGNLLEKIAGQLGERGKKSQTLSQELDEAGFVS

YLGDKENWWIGLSKEKQGSFTIPYYVLGQAWQIFISDQPLDGLVVTPFEAFYQEHFERWKLNAEKTLFYGSV

NLQQSESLFAYYEPIYRVIIQGNLNQIVEELNLLEKVVLENTPRIPITKQLFIQFVMDVFHLFEHLKADDMT

DIVKTIHAIQSFDELVSYIKETLISFFGQYRMNENVVSVLEVIGRDYQKELSLKDISKALFINPVYLGQLIK

RETDSTFAELLNKQRIKAAQQLLLSTSDSIENICYAVGYSNLGYFYKVFRKLCGKSPKAYRKQVETIL

-COOH (E) Polynucleotide sequence from *Streptococcus pneumoniae* Histidine
Kinase [SEQ ID NO:5], cognate of the Response Regulator of the invention.
5'-

CTTATATGCAGAACATGGTTATAGCTTTCGGGAATACAGTTTGAAGGAGGCTTGGTCTCTTTACAAGCAAAA

TTTTATCTCAAGCAACCTGATTTTCTATAGCTTTTTAGGTGTGGGTCTAGTTTTGACCTATGGTTTGTATCT

CTTGGTGCAATTGCCTCATCAGACCATTGTTCATTTGATTGCGACCCTTTTGAATGTCCTAGTAGTTGCCCT

GATCTTTTTGGCTTATACAGTATCTTTAAAATTACAAGTTTATTTTGCCTTGTCCTATCGAAATAGTCTCAA

ATTATCCTTGATTGGCATCTTTATGAGTCTAGCAGCTGTGGCTAAGGTTCTCCTTGGGACTGTGCTACTTGT

AGCAATTGGTTACTATATGCCTGCCCTGCTATTTTTTGTAGGAATTGGGATGTGGCATTTCTTTATCAGTGA

TATGTTGGAACCTGTCTATGAAATCATCCATGAAAAATTGGCGACAAAATAGAATGAAGCACTTTTGGCTAC

ATACGCTTCTAAGAACCTATAGTTCAGTGATGATCAGTATCATTGCGAGTTTTGCAATCTTACTCTCTTACG

CTGACTGGGATTCACGTGAAAAGGAAGCCCAGAGAGTAGCCCAGCGTGTAACTGCTAGAACAGTGAGTGAAA

TTGAATATTACCATAGAGAGTCAACCCAGATAGCTCAGGCTTTAGTTGAAAACCAAGCTCGTATTGAGGGAA

TCTATAAATACTTTAGCCTTAGCATGCCAGACTATTTTTACTGGCAATTAGAGCGGAAAGCTTCGCCTTATA

TATCAGTCTCTCTGTATCAAAATGTTGATGACCTCTATGTTCGAAATGATTTTGTAACTGGGGTGGCCATTG

TCTTTCAAGATTACAAGGAAGTCTATGTTTCTACTAAAGACAAACGTAGTGGAGAAAAAATCAGGGCTGAGG

ATTTCAAACCAGCAGGAAATAGTTTTGCCATTCCAGTGTCAGATCCAGTGTCAGATCAAGACTTAGGAGTGA

TTTACATCTCCTTGGATCCTGCTGTTTTATACCATGCCATTGATAATACTAGAGGTCATACTCCGATGGCAG

TAACAGTGACCGAACCTTTTGATACGGAGATTTTTCATATTGGTGAGACAGTTGATAAGGAGAGTGAAAATT

GGCTAGTTGGCTTAACTTCTCATGGTTATCAGGTTCAGGTGGCAGTTCCCAAAAACTTTGTTTTACAAGGAA

CGGTGACCAGCTCTGCTTTGATTGTGGGCTTGAGCCTTCTCTTTATTGTCATTCTTTATCTGACTTTGAGGC

TABLE 1-continued

Response regulator Polynucleotide and Polypeptide Sequences

```
AGACCTTTGCTAATTATCAAAAGCAGGTAGTGGATTTGGTGGATTCCATCCAAGCTATTGCCCAAGGACAAG
AAGGTCTTCGCATTGATACGCTTGAAAAGGATCAGGAATTGCTCCTAATCGCGGAGACGACCAATGATATGT
TGGATCGATTGGAAAAGAATATCCATGATATTTACCAGTTAGAACTCAGTCAAAAAGATGCCAATATGCGGG
CCTTGCAGGCGCAAATCAATCCTCATTTTATGTATAATACGCTGGAGTTCTTGCGCATGTATGCAGTTATGC
AGAGTCAAGATGAGTTGGCAGATATCATTTATGAATTCAGTAGTCTCTTGCGTAACAATATTTCCGACGAAA
GAGAGACCCTCCTCAAACAGGAATTAGAATTTTGCCGTAAATACAGCTATCTCTGCATGGTTCGCTATCCCA
AGTCCATTGCCTATGGTTTCAAGATAGATCCAGAGTTAGAGAATATGAAGATTCCCAAGTTTACCTTGCAAC
CGCTGGTAGAAAACTATTTCGCGCATGGTGTTGACCACAGGCGGACAGATAATGTGATTAGCATCAAGGCTC
TTAAACAGGATGGTTTTGTGGAAATTTTGGTGGTCGATAATGGTAGAGGAATGTCGGCTGAAAAGTTGGCAA
ATATCCGAGAAAAATTAAGTCAGAGATATTTTGAACACCAAGCCAGCTACAGTGATCAAAGGCAGTCTATCG
GGATTGTCAATGTACACGAGCGTTTTGTGCTCTATTTTGGAGACCGCTATGCCATTACTATAGAGTCTGCAG
AGCAAGCCGGTGTTCAGTATCGTATTACAATTCAAGATGAGTAGAAAGGGAGAAAATGTATAAAGTATTATT
AGTAGATGATGAGTACATGGTGACAGAAGGTCTGAAGCGTTTGATTCCCTTTGATAAGTGGGATATGGAGGT
CGTCGCAACAGTCAGTCATGCCGATGAAGCTCTAGAATATGTTCAGGAAAATCCTGTCGATGTCATCATTTC
CGATGTCAATATGCCAGACAAAACAGGGCTTGATATGATTCGGGAGATGAAAGAGATCTTACCAGATGCTGC
CTATATCCTGCTCTCAGGTTATCAGGAGTTTGATTATGTAAAAAGAGCAATGAATCTTAGTGTGGTGGACTA
TTTGGTCAAACCTGTTGATAAGGTAGAGCTGGGAAATCTGCTGGAGAAGATTGCAGGTCAGCTCGGCGAGAG
AGGGAAGAAAAGTCAGACTCTTAGTCAAGAATTAGACGAGGCTGGATTTGTTAGTTATTTAGGGGATAAGGA
GAATTGGTGGATAGGTCTATCCAAGGAAAAACAAGGTTCCTTCACCATTCCCTACTATGTCTTGGGTCAAGC
CTGGCAGATTTTCATTTCTGACCAACCCCTAGATGGTTTAGTCGTTACACCTTTTGAAGCTCCTTATCAAGA
ACATTTTGAACGCTGGAAGCTGAATGCTGAGAAAACCCTCTTTTACGGTTCTGTAAATCTGCAGCAGTCTGA
GAGTCTCTTTGCCTATTACGAACCGATTTATAGGGTTATCATTCAGGGAAATCTCAATCAAATCGTAGAAGA
GTTAAATCTCTTGGAGAAGGTAGTTCTTGAAAATACGCCGCGAATTCCGATTACTAAACAGCTTTTTATCCA
GTTTGTCATGGATGTCTTCCATTTATTTGAACATCTCAAAGCTGATGATATGACGGACATTGTCAAAACCAT
TCATGCTATTCAATCCTTCGATGAATTGGTTTCTTATATCAAGGAAACTCTGATCAGCTTTTTCGGTCAATA
CCGTATGAATGAAAATGTGGTCAGTGTGCTGGAAGTCATTGGTCGTGATTACCAAAAAGAGCTTTCCCTCAA
GGATATCAGTAAGGCCCTCTTTATCAATCCTGTCTATCTAGGGCAGTTGATTAAGCGTGAAACCGATTCGAC
CTTTGCAGAGTTACTAAACAAACAACGTATTAAGGCTGCCCAACAACTTTTGCTTTCAACTAGTGACAGCAT
CGAAAATATTTGTTATGCTGTTGGTTACAGTAACCTTGGATATTTCTATAAAGTTTTCCGAAAATTGTGCGG
AAAATCGCCAAAAGCCTACCGAAAACAGGTAGAAACTATACTATAAGATTTGTATTCCTTTACAAAATG
```
-3'

(F) Polypeptide sequences from Streptococcus pneumoniae Histidine
Kinase [SEQ ID NO:6] deduced from the polynucleotide of SEQ ID NO:5,
cognate of the Response Regulator of the invention.
NH₂-

MKSSMKNWRQNRMKHFWLHTLLRTYSSVMIIIIASFAILLSYADWDSREKEAQRVAQRVTARTVSEIEYY

HRESTQIAQALVENQARIEGIYKYFSLSMPDYFYWQLERKASPYISVSLYENVDDLYVRNDFVTGVAIAF

QDYKEVYVSTKDKRSGEKIRAEDFKPAGNSFAIPVSDFVSDQDLGVIYISLDPAVLYHAIDNTRGHTPMA

VTVTEPFDTEIFHIGETVDKESENWLVGLTSHGYQVQVAVPKNFVLQGTVTSSALIVGLSLLFIVILYLT

LRQTFANYQKQVVDLVDSIQAIAQGQEGLRIDTLEKDQELLLIAETTNDMLDRLEKNIHDIYQLELSQKD

TABLE 1-continued

Response regulator Polynucleotide and Polypeptide Sequences

ANMRALQAQINPHFMYNTLEFLRMYAVMQSQDELADIIYEFSSLLRNNISDERETLLKQELEFCRKYSYL

CMVRYPKSIAYGFKIDPELENMKIPKFTLQPLVENYFAHGYDHRRTDNVISIKALKQDGFVEILVVDNGR

GMSAEKLANIREKLSQRYFEHQASYSDQRQSIGIVVVHERFVLYFGDRYAITIESAEQAGVQYRITIQDE

-COOH

Deposited materials

A deposit containing a Streptoccus pneumoniae 0100993 strain has been deposited with the National Collections of Industrial and Marine Bacteria Ltd. (herein "NCIMB"), 23 St. Machar Drive, Aberdeen AB2 1RY, Scotland on Apr. 11, 1996 and assigned deposit number 40794. The deposit was described as Streptococcus pneumoniae 0100993 on deposit. On Apr. 17, 1996 a Streptococcus pneumoniae 0100993 DNA library in E. coli was similarly deposited with the NCIMB and assigned deposit number 40800. The Streptococcus pneumoniae strain deposit is referred to herein as "the deposited strain" or as "the DNA of the deposited strain."

The deposited strain contains a full length Response regulator gene. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The deposited strain will be irrevocably and without restriction or condition released to the public upon the issuance of a patent. The deposited strain is provided merely as convenience to those of skill in the art and is not an admission that a deposit is required for enablement, such as that required under 35 U.S.C. §112. A license may be required to make, use or sell the deposited strain, and compounds derived therefrom, and no such license is hereby granted.

In one aspect of the invention there is provided an isolated nucleic acid molecular encoding a mature polypeptide expressible by the Streptococcus pneumoniae 0100993 strain, which polypeptide is contained in the deposited strain. Further provided by the invention are Response regulator polynucleotide sequences in the deposited strain, such as DNA and RNA, and amino acid sequences encoded thereby. Also provided by the invention are Response regulator polypeptide and polynucleotide sequences isolated from the deposited strain.

Polypeptides

Response regulator polypeptide of the invention is substantially phylogenetically related to other proteins of the response regulator family.

In one aspect of the invention there are provided polypeptides of Streptococcus pneumoniae referred to herein as "Response regulator" and "Response regulator polypeptides" as well as biologically, diagnostically, prophylactically, clinically or therapeutically useful variants thereof, and compositions comprising the same.

Among the particularly preferred embodiments of the invention are variants of Response regulator polypeptide encoded by naturally occurring alleles of the Response regulator gene. The present invention further provides for an isolated polypeptide which: (a) comprises or consists of an amino acid sequence which has at least 70% identity, preferably at least 80% identity, more preferably at least 90% identity, yet more preferably at least 95% identity, most preferably at least 97–99% or exact identity, to that of SEQ ID NO: 2 over the entire length of SEQ ID NO:2; (b) a polypeptide encoded by an isolated polynucleotide comprising or consisting of a polynucleotide sequence which has at least 70% identity, preferably at least 80%; identity, more preferably at least 90% identity, yet more preferably at least 95% identity, even more preferably at least 97–99% or exact identity to SEQ ID NO:1 over the entire length of SEQ ID NO:1; (c) a polypeptide encoded by an isolated polynucleotide comprising or consisting of a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:2, over the entire length of SEQ ID NO:2, or (d) a polypeptide encoded by an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity, to SEQ ID NO:1 over the entire length of SEQ ID NO:3; (e) a polypeptide encoded by an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity to SEQ ID NO:3 over the entire length of SEQ ID NO:3; or (f) a polypeptide encoded by an isolated polynucleotide comprising or consisting of a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:4, over the entire length of SEQ ID NO:4; (g) comprises or consists of an amino acid sequence which has at least 70% identity, preferably at least 80% identity, more preferably at least 90% identity, yet more preferably at least 95% identity, most preferably at least 97–99% or exact identity, to the amino acid sequence of SEQ ID NO:2 over the entire length of SEQ ID NO:4.

The polypeptides of the invention include a polypeptide of Table 1 [SEQ ID NO:2 or 4] (in particular the mature polypeptide) as well as polypeptides and fragments, particularly those which have the biological activity of Response resultor, and also those which have at least 70% identity to a polypeptide of Table 1 [SEQ ID NO:1 or 3]or the relevant portion, preferably at least 80% identity to a polypeptide of Table 1 [SEQ ID NO:2 or 4] and more preferably at least 90% identity to a polypeptide of Table 1 [SEQ ID NO:2 or 4] and still more preferably at least 95% identity to a polypeptide of Table 1 [SEQ ID NO:2 or 4] and also include portions of such polypeptides with such portion of the polypeptide generally containing at least 30 amino acids and more preferably at least 50 amino acids.

The invention also includes a polypeptide consisting of or comprising a polypeptide of the formula:

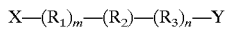

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof. In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from Streptococcus pneumoniae, however, it may preferably be obtained from other organisms of the same taxonomic genus. A polypeptide of the invention may also be obtained, for example, from organisms of the same taxonomic family order.

A fragment is a variant polypeptide having an amino acid sequence that is entirely the same as part may not all of any amino acid sequence of any polypeptide of the invention. As with Response regulator polypeptides, fragments may be "free-standing" or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2 or 4], or of variants thereof, such as a continuous series of residues that includes an amino- and/or carboxyl-terminal amino acid sequence. Degradation forms of the polypeptides of the invention produced by or in a host cell, particularly a Streptococcus pneumoniae, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO:2, or an isolated polypeptide comprising an amino acid sequence having at least 15, 20, 30, 40, 50 or 100 contiguous amino acids truncated or deleted from the amino acid sequence of SEQ ID NO:2.

Also preferred are biologically active fragments which are those fragments that mediate activities of Response regulator, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of Streptococcus pneumoniae or the ability to initiate, or maintain cause Disease in an individual, particularly a human.

Fragments of the polypeptides of the invention may be employed for producing the corresponding full-length polypeptide by peptide synthesis; therefore, these variants may be employed as intermediates for producing the full-length polypeptides of the invention.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

Polynucleotides

It is an object of the invention to provide polynucleotides that encode Response regulator polypeptides, particularly polynucleotides that encode the polypeptide herein designated Response regulator.

In a particularly preferred embodiment of the invention the polynucleotide comprises a region encoding Response regulator polypeptides comprising a sequence set out in Table 1 [SEQ ID NO:1 or 3] which includes a full length gene, or a variant thereof. The Applicants believe that this full length gene is essential to the growth and/or survival of an organism which possesses it, such as Streptococcus pneumoniae.

As a further aspect of the invention there are provided isolated nucleic acid molecules encoding and/or expressing Response regulator polypeptides and polynucleotides, particularly Streptococcus pneumoniae Response regulator polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a Response regulator polypeptide having a deduced amino acid sequence of Table 1 [SEQ ID NO:2 or 4] and polynucleotides closely related thereto and variants thereof.

In another particularly preferred embodiment of the invention there is a Response regulator polypeptide from Streptococcus pneumoniae comprising or consisting of an amino acid sequence of Table 1 [SEQ ID NO:2 or 4], or a variant thereof.

Using the information provided herein, such as a polynucleotide sequence set out in Table 1 [SEQ ID NO:1 or 3], a polynucleotide of the invention encoding Response regulator polypeptide may be obtained using standard cloning and screening methods, such as those for cloning and sequencing chromosomal DNA fragments from bacteria using Streptococcus pneumoniae 0100993 cells as starting material, followed by obtaining a full length clone. For example, to obtain a polynucleotide sequence of the invention, such as a polynucleotide sequence given in Table 1 [SEQ ID NO:1 or 3], typically a library of clones of chromosomal DNA of Streptococcus pneumoniae 0100993 in E.coli or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL*, 2nd Ed.; Cold Spring Harbor Laboratory Press, Cold Spring Harbor, N.Y. (1988). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in Table 1 [SEQ ID NO:1 or 3] was discovered in a DNA library derived from Streptococcus pneumoniae 0100993.

Moreover, each DNA sequence set out in Table 1 [SEQ ID NO:1 or 3] contains an open reading frame encoding a protein having about the number of amino acid residues set forth in Table 1 [SEQ ID NO:2 or 4] with a deduced molecular weight that can be calculated using amino acid residue molecular weight values well known to those skilled in the art. The polynucleotide of SEQ ID NO:1, between nucleotide number 2144 and the stop codon which begins at nucleotide number 3428 of SEQ ID NO:1, encodes the polypeptide of SEQ ID NO:2. The polynucleotide of SEQ ID NO:5, between nucleotide number 450 and the stop codon which begins at nucleotide number 2130 of SEQ ID NO:5, encodes thepolypeptide of SEQ ID NO:6.

In a further aspect, the present invention provides for an isolated polynucleotide comprising or consisting of: (a) a polynucleotide sequence which has at least 70% identity, preferably at least 80% identity, more preferably at least 90% identity, yet more preferably at least 95% identity, even more preferably at least 97–99% or exact identity to SEQ ID NO:1 over the entire length of SEQ ID NO:1; (b) a polynucleotide sequence encoding a polypeptide which has at least 70% identity, preferably at least 80% identity, more preferably at least 90% identity, yet more preferably at least 95% identity, even more preferably at least 97–99% or 100% exact, to the amino acid sequence of SEQ ID NO:2, over the entire length of SEQ ID NO:2; or (c) a nucleotide sequence which has at least 70% identity, preferably at least 80% identity, more preferably at least 90% identity, yet more preferably at least 95% identity, even more preferably at least 97–99% or 100% identity, to SEQ ID NO:1 over the entire length of SEQ ID NO:3; (d) a nucleotide sequence which has at least 70% identity, preferably at least 80% identity, more preferably at least 90% identity, yet more preferably at least 95% identity, even more preferably at least 97–99% or exact identity to SEQ ID NO:3 over the entire length of SEQ ID NO:3; or (e) a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:4, over the entire length of SEQ ID NO:4.

A polynucleotide encoding a polypeptide of the present invention, including homologs and orthologs from species other than Streptococcus pneumoniae, may be obtained by a process which comprises the steps of screening an appropriate library under stringent hybridization conditions with a labeled or detectable probe consisting of or comprising the sequence of SEQ ID NO:1 or 3 or a fragment thereof; and isolating a full-length gene and/or genomic clones containing said polynucleotide sequence.

The invention provides a polynucleotide sequence identical over its entire length to a coding sequence (open reading frame) in Table 1 [SEQ ID NO:1 or 3]. Also provided by the invention is a coding sequence for a mature polypeptide or a fragment thereof, by itself as well as a coding sequence for a mature polypeptide or a fragment in reading frame with another coding sequence, such as a sequence encoding a leader or secretary sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide 2144 to the nucleotide immediately upstream of or including nucleotide 3428 set forth in SEQ ID NO:1 of Table 1, both of which encode the Response regulator polypeptide.

The invention also includes a polynucleotide consisting of or comprising a polynucleotide of the formula:

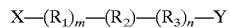

$$X-(R_1)_m-(R_2)-(R_3)_n-Y$$

wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from Streptococcus pneumoniae, however, it may preferably be obtained from other organisms of the same taxonomic genus. A polynucleotide of the invention may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the Streptococcus pneumoniae. Response regulator having an amino acid sequence set out in Table 1 [SEQ ID NO:2 or 4]. The term also encompasses polynucleotides that include a single continuous region or discontinuous regions encoding the polypeptide (for example, polynucleotides interrupted by integrated phage, an integrated insertion sequence, an integrated vector sequence, an integrated transponson sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of Table 1 [SEQ ID NO: 2 or 4]. Fragments of a polynucleotides of the invention may be used, for example, to synthesize full-length polynucleotides of the invention.

Further particularly preferred embodiments are polynucleotides encoding Response regulator variants, that have the amino acid sequence of Response regulator polypeptide of Table 1 [SEQ ID NO:2 or 4] which several, a few, 5 to 10, 1 to 5, 3, 2, 1 or no amino acid residues are substituted, modified, deleted and/or added, in any combination. Especially preferred among these are silent substitutions, additions and deletions, that do not alter the properties and activities of Response regulator polypeptide.

Further preferred embodiments of the invention are polynucleotides that are at least 70% identical over their entire length to a polynucleotide encoding Response regulator polypeptide having an amino acid sequence set out in Table 1 [SEQ ID NO:2 or 4], and polynucleotides that are complementary to such polynucleotides. Alternatively, most highly preferred are polynucleotides that comprise a region that is at least 80% identical over its entire length to a polynucleotide encoding Response regulator polypeptide and polynucleotides complementary thereto. In this regard, polynucleotides at leas 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of Table 1 [SEQ ID NO:1 or 3].

In accordance with certain preferred embodiments of this invention there are provided polynucleotides that hybridize, particularly under stringent conditions, to Response regulator polynucleotide sequences, such as those polynucleotides in Table 1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5× SSC (150 mM NaCl, 15 mM trisodium citrate), 50 mM sodium phosphate (pH 7.6), 5× Denhardt's solution, 10% dextran sulfate, and 20 micrograms/ml of denatured, sheared salmon sperm DNA, followed by washing the hydridization support in 0.1×0 SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriate library containing the complete gene for a polynucleotide sequence set forth in SEQ ID NO:1 or 3 under stringent hybridization conditions with a probe having the sequence of said polynucleotide sequence set forth in SEQ ID NO:1 or 3 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding Response regulator and to isolate cDNA and genomic clones of other genes that have a high identity, particularly high sequence identity, to the Response regulator gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have lee than 30 nucleotide residues or base pairs.

A coding region of a Response regulator gene may be isolated by screening using a DNA sequence provided in Table 1 [SEQ ID NO:1 or 3] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length CNAs, or extend short DNAs, for example those based on the method of Rapid Amplification of cDNA ends (RACE) (see, for example, Frohman, et al., *PNAS USA* 85: 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the selected gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of Table 1 [SEQ ID NOS:1 or 2 or 3 or 4] may be used in the process herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature forms has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems which comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides or the invention. Introduction of a polynucleotide into the host cell can be effected by methods described in many standard laboratory manuals, such as Davis, et al., *BASIC METHODS IN MOLECULAR BIOLOGY,* (1986) and Sambrook, et al., *MOLECULAR CLONING: A LABORATORY MANUAL,* 2nd Ed., Cold Spring Harbor Laboratory Press, Cold Spring Harbor, N.Y. (1989), such as, calcium phosphate transfection, DEAE-dextran mediated transfection, transvection, microinjection, cationic liquid-mediated transfection, electroporation, transduction, scrape loading, ballistic introduction and infection.

Representative examples of appropriate hosts include bacterial cells, such as cells of streptococci, straphylococci, enterococci *E. coli,* streptomyces, cyanobacteria, *Bacillus subtilis,* and Streptococcus pneumoniae; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such s baculoviruses, papova viruses, such as SV40, vaccinia viruses, adenoviruses, fowl pox viruses, pseudorabies viruses, picornaviruses and retroviruses, and vectors derived from combinations thereof, such as those derived from plasmid and bacteriphage genetic elements, such as cosmids and phagemids. The expression system constructs may contain regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL,* (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of Response regulator polynucleotides and polypeptides of the invention for use as diagnostic reagents. Detection of Response regulator polynucleotides and/or polypeptids in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the Response regulator gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of those sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplificiation, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled Response regulator polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetcis. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as RNase, V1 and S1 protection assay or a chemical cleavage method. See, for example, Cotton et al., *Proc. Natl. Acad. Sci., USA*, 85: 4397–4401(1985).

In another embodiment, an array of oligonucleotides probes comprising Response regulator nucleotide sequence of fragments thereof can be constructed to conduct efficient screening of, for example, genetic mutations, serotype, taxonoic classification or identification. Array technology methods are well known and have general applicability and can be used to address a variety of questions in molecular genetics including gene expression, genetic linkage, and genetic variability (see, for example, Chee et al., *Science*, 274: 610(1996)).

Thus in another aspect, the present invention relates to a diagnostic kit which comprises: (a) a polynucleotide of the present invention, preferably the nucleotide sequence of SEQ ID NO:1 or 3, or a fragment thereof; (b) a nucleotide sequence complementary to that of (a); (c) a polypeptide of the present invention, preferably the polypeptide of SEQ ID NO:2 or 4 or a fragment thereof; or (d) an antibody to a polypeptide of the present invention, preferably to the polypeptide of SEQ ID NO:2 or 4.

It will be appreciated that in any such kit (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NO:1 or 3, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The nucleotide sequences of the present invention are also valuable for organism chromosome identification. The sequence is specifically targeted to, and can hybridize with, a particular location on an organism's chromosome, particularly to a Streptococcus pneumoniae chromosome. The mapping of revlevant sequences to chromosomes according to the present invention may be an important step in correlating those sequences with pathogenic potential and/or an ecological niche of an orgarism and/or drug resistance of an organism, as well as the essentiality of the gene to the organism. Once asequence has been mapped to aprecise chromosomal location, the physical position of the sequence on the chromsome can be correlated with genetic map data. Such data may be found on-line in a sequence database. The relationship between genens and deiseases that have been mapped to the same chromomosomal region are then identified through known genetic methods, for example, through linkage analysis (coinheritance of physically adjacent genes) or mating studies, such as by conjugation.

The differences in a polymucleotied and/or polypeptide sequence between organisms possessing first phenotype and organisms possesing a different, second different phenotype can also be determined. If a mutation is oberved in some or all organisms possessing the first phenotype but not in any organisms possesing the second phenotype, then the mutations is likely to be the causative agent of the first phenotype.

Cell from an organism carring mutations ot polymorphisms (allelic variations) in a polynucleotide and/or polypeptide of the ivention may also be detected at the polymucleotide or polypeptide level by a variety of techniques, to allow for serotyping for example. For example, RT-PCR can be used to detect mutaitons in the RNA. It is particularly preferred to use RT-PCR in conjunction with automated detection systems, such as, for example, GeneScan. RNA,cDna or genomic DNA may also be used for the same purpose, PCR. As an example PCR primers complementary to a polynucleotide encoding Response regulator polypeptide can be used to identify and analyze nutations. Examples of representative primers are shown below in Table 2.

TABLE 2

Primers for amplification of Response regulator polynucleotides

| SEQ ID NO | PRIMER SEQUENCE |
|---|---|
| 7 | 5'-ATGTATAAAGTATTATTAGTAGATG-3' |
| 8 | 5'-TAGTATAGTTTCTACCTGTTTTCGG-3' |

The invention also includes primers of the formula:

$$X-(R_1)_m-(R_2)-(R_3)_n-Y$$

wherein, at the 5' end of the moleule, X is hydrogen, an metatl or a modified nucleotide residue, and at the 3' end of the molecule, Y is hydrogen, a metal or a modified nuleotide residue, $R_1$ and $R_3$ are any nucleic acid residue or modified nucleotide residue, m is an integer between 1 and 20 or zero, n is an integer between 1 and 20 or zero, and $R_2$ is a primer sequence of the invention, particularly a primer sequence selected from Table 2. In the polymucleotide formula above $R_2$ is oriented so the its 5' end nucleotide residue is at the left, bound to $R_1$, and its 3' end nucleotide residue is at the right, bound to $R_3$. Any stretch of nucleic acid residures denoted by either R group, where m and/or n is greater then 1,may be either a heteropolymer or a homopolymer, preferably a heteropolymer being complementary to a region of a polymucleotide of Table 1. In a preferred embodiment m and/or n is and integer between 1 and 10.

The invention further provides these primers with 1,2,3,or 4 nucleotides removed from the 5' and/or the 3' end. These primers may be used for, among other things, amplifying Resopnse regulator DNA and/or RNA isltated from a sample derived from an individual, such as abody material. The primers may be used to amplify a polynucleotide isolated from an infected individual, such that the polynucleotide may then be subject to various techniques for elucidation of the polyncleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferablu bacterial infections, ore preferably infections caused by *Strepococcus pneumoniae*, comprising determining from a smaple derived from an individual, such as a bodily material, an increased level of expression of polynucleotide having a sequence of Table 1 [SEQ ID NO:1 or 3]. Increased or decreased expression of a Response regulator polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detection over-expression of Response regulator polypeptide compared to normal control tissue samples may be used to dtect the presence of and ifection, for example. Assay techniques that can be used to determine levels of a Response regulator polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Differential Expression

The polynucleotides and polynucleotides of the invention may be used as reagents for differential screening methods.

There are many differentail screening and differential display methods known in the art in which the polynucleotides and ploypeptides of the invention may be used. For example, the differential display technique is described by Chuang et al., *J. Bacteriol.* 175:2026–2036 (1993). This method identifies those genes which are expressed in an organisim by identifying mRNA present using randomly-primed RT-PCR. By comparing pre-infection and post infection profiles, genes up and down regulated during infection can be identified and the RT-PCR product sequenced and matched to ORF "unknowns."

In Vivo Expression Technology (IVET) is described by Camilli et al., *Proc. Nat'l Acad Sci.* USA 91:2634–2638 (1994). IVET identifies genes up-regulated during infection when compared to laboratory cultivation, implying an important role in infection. ORFs identified by this technique are implied to have a significant role in infection establishment and/or maintenance. In this technique random chromosomal fragments of target organism are cloned upstream of a promoter-less recomdinase gene in a plasmid vector. This contruct is introduced into the target organism which carries an antibiotic resistance gene flanked by resolvase sites. Growth in the presence of the antibiotic removes from the po;ulation those fragements cloned into the plasmid vector capable of suppoting transcription of the recombinase gene and therfore have caused loss of anitbiotic resistance. The resistant pool is introduced into a host and at various times after infection bacteria may be recovered and assessed for the presence of anitibiotic resistance. The chromosomal fragment carred by each anibiotic sensitive bacterium should carry a promoter or portion of a gene normally upregulated during infection. Sequencing upstream of the recombinase gene allows identification of the up regulated gene.

RT-PCR may also be used to analyze gene expression patterns. For RT PCR using the polynucleotides of the invention, messager RNA is isolated from bacterial infected tissue, e.g., 48 hour murine lung infections, and the amount of each mRNA species assessed by reverse transcription of the RNA sample primed with random hexanucleotides followed by PCR withgene specific primer pairs. The determination of the presence and amount of a particular mRNA species by quantifaction of the resultant PCR product provides information on the bacterial genes which are transcribed in the infected tissue. Analysis of gene transcription can be carried out a different times of infection to gain a detailed knowledge of gene regulation in bacterial pathogenesis allowing for a clearer undersatanding of which gene products represent target for screen for anibacterials. Because of the gene specific nature of the PCR primers employed it should be understood that the bacterial mRNA prepartion need not be free of mammalian RNA. This allows the investigator to carry out a simple and quick RNA preparation from infected tissue to obtain bacterial mRNA speices which are bery short lived in the bacterium (in the order of 2 minute halfives). Optimally the bacterial mRNA is prepared from infected murine lung tissue by mechanical disruption in the presence of TRIzole (GIBCO-BRL) for very short periods of time, subsequent processing according to the manufacturers of TRIzole regent and DNAase treatment to remove contaminating DNA. Preferably the processsis optimized by finding those conditions which give a maximum amount of *Streptococcus pneumoniae* 16S ribosomal RNA as detected by probing Northerns with a suitably lableed sequence specific oligonucleotide probe. Typically a 5' dye labeled primer is used in each PCR primer pair in aPCR recaction which is terminated optimally between 8 and 25 cycles. The PCR products are separated on 6% polyacylamide gels with detection and quantification using GeneScanner (manufactured by ABI).

Gridding and Polynucleotide Subtraction

Methods have been described for obtaining information about gene expression and identity using so called "high density DNA arrys" or gids. See, e.g., M. Chee et al., Science, 274:610–614 (1996) and other refences cited therein. Such gridding assays have been employed to identitfy certain novel gene sequences, referred to as Expressed Sequence Tags (EST) (Adams et a., Science,252:1651–1656 (1991)). A varietyof techniques have also been described for identifying particular gene sequences on the basis of their gene products. For example, see International Patent Application No. W091/107087, published May 30, 1991. In addition, methods have been described for the amplicafication of desired sequences. For example, see International Patent Application No. W091/17271, published Nov. 14, 1991.

The polynucleotides of the invention amy be used as components of polynucleotide arrys, preferably high density arrays or grids. These high density arrays are particularly useful for diagnostic and prognostic purposes. For example, a set of sposts each comprising a different gene, and further comprisninga a polyncleotide or polydnucleotides of the invention, may be used for probing, such as using hybridization or nucleic amplification, using a probes obatianed or derived from a bodily sample, to determaine the presence of a particular polyncleotide sequence or related sequence in an individual. Such a presence may idicated the presence of a pathogen, Particularly Steptococcus pneumoniae, and may be useful in diagnosing and/or prognosing disease or a course disease. A grid comprising a number of variants of the polynucleotide sequence of SEQ ID NO:1 or 3 are preferred. Also preferred is a comprising a number of variants of a polynucleotide sequence encoding the polypeptide sequence of SEQ ID NO:2 or 4.

Antibodies

The polypeptides and polyuncleotides of the invention or variants thereof, or cells expressing the same can be used as immunogens to produce antibodies immunospecific for such polypeptides or polynucleotides respectivelty.

In certain preferred embodiments of the invention there are provided antibodies against Response regulator polypeptides or polynucleotides.

Antibodies generated against the polypeptides or polynucleotides of the invention can be obtained by administering the polypeoptides and/or polynucleotides of the invention, or epitiope-bearing fragments of either or both, analoues of either or both, or cells expressing eithr or both, to an animal, preferably a nonhuman, using routine protocols. For preparation of monoclonal antibodies, any technique known in the art that provides antibodies produced by continous cell line cultures can be used. Examples include various techniques, such as those in Kohler, G. and Milstein, C., Nature 256: 495–497 (1975); Kozbor et al., Innunology Today 4: 72 (1983); Cole et al., pg. 77–96 in MONOCLONAL ANTIBODIES AND CANCER THERAPY, Alan R. Liss, Inc. (1985).

Techniques for the production of signle chain antibodies (U.S. Pat. No. 4,946,778) can be adpated to produce single chain antibodies to polypeptides or polynucleotides of this invention. Also, transgenic mice, or other organisms such as other mammals, may be used to express humanized antibodies immuospecific to the polypeptides or polynucleotides of the invention.

Alternatively, phage display technology may b eutilized to select antibody genes with binding acitivities towards a polypeptide of the invention their from repetoires of PCR amplified v-genes of lymphotocytes from humans screened form possesing anti-Respones regulator or from naive libraries (McCafferty, et al., (1990), Nature 348, 522–554; Marks, et al., (1992) Biotechnology 10, 779–783). The affinity of these andibodies can also be improved by, for example, chain shuffling (Clackson et al., (1991) Nature 252:628).

The above-described antibodies may be employed ti isolate or to identify clones expressing the polypeptides or polynulceotides of the invention to purify the polypeptides or polynucleotides by, for example, affinity chromoatography.

Thus, among others, antibodies against Response regulato-polypeptide or Response regulator-polynucleotide may be employed to treat infections, particularly bacterial infections.

Polypepetide variants include antigenically, epitopically or immunologically equivalent variants form a particular aspect of this invention.

A polypeptide or polyncleotide of the ivention, such as an antigenically or immunologically equivalent derivatiive or a fusing protein of the polypeptide is used as an antigen to immunize a mousee or toher animal such as a rat chicken. The fusion protein may provide stablity to the polypeptide. The natigen may be associated for example by conjugation, with an immunogenic carrier protein for exmaple bovine serum albumin, keyhole limpet haemcyanin or tetanus toxoid. Alternatively, a multiple antigenic polypeptide comprising mulitple copies of the polypeptide, or an antigenically or immunolgically equivalent polypeptide thereof may be sufficently antigeic to improve immunogenicity so as to obviate the use of a carrier.

Preferably, the antibody or variant thereof is modified to make it less immunogenic in the individual. For example, if the individual is human the antibody may most preferably be "humanized," where the complimentarity determining region or regions of the hybirdoma-derived antibody has been transplatedinto a human monoclonal anitbody, for example as described in Jones et al. (1986), Nature 321, 522–525 or Tempset et al., (1991) Biotechnology 9, 266–273.

In accordance with an aspect of the invention, there is provided the use of a polynucleotide of the invention for therapeutic or prophylactic purposes, in particular genetic immunization. Among the particularly preferred embodiments of the invention are naturally occurring allelic variants of Response regulator polynucleotides and polypeptides encoded thereby.

The use of a plynucleotide of the invention in genetic immuization will preferably employ a suitable delivery method such as direct injection of plasmid DNA into muscles (Wolff et al., Hum Mol Genet (1992) 1:363, Manthorpe et al., Hum. Gene Ther. (1983)4: 419), delivery of DNA complexed with specific protein carriers (Wu et al., J Biol Chem. (1989) 264: 16985), corpecipiation of DNA with calcium phoshate (Benvenisty & REshef, PNAS USA, (1986) 83 : 9551), encapsulation of DNA in various forms of lipsomers (Kaneda et al., Science (1989) 243: 375), particle bombardment (Tang et al., Nature (1992) 356:152, Eisenbraun et al., DNA Cell Biol (1993) 12: 791) and in vivo infection using cloned retrovial vectors (Seeger et al., PNAS USA (1984) 81:5849).

Polypeptides and plynucleotides of the invention may also be used to assess the binding of small molecule substrates and ligands in, for example, cells, cell-free preparation, chemical libraries, and natural product mixtures. These substrates and ligands may be natural substantes and ligands or may be structural or fuctional mimetics. See, e.g., Soligan et al, *Current Protocols I Immunology* 1 (2): Chapter 5 (1991).

Polypeptides and polynucleotides of the present invention are responsible for amny biological functions, including many disease states, in partivular the Diseases hereinbefore mentioned. It is therefore disirable to devise screening mathods to idenfity compounds which stimulate or which inhibit the functon of the polypetides or polynucleotide. Accordingly, in a afurther speect, the present invention provides for method of screening compounds to identify those which stimulate or which inhibit the function of a polypeptide or polynuleotidesof the invention, as well as related polypeptides and polynucleoties. In greral, agonists or antagonists may be emploued for therapteutic and prophylactic purpose for such Diseases as hereinbefore mentioneed. Compounds may be identified from a variety of sourecs, for example, cell, cell-free prepaartions, chemcial libraries, and natural product mixtures. Such agonists, andagonistis or inhibitor so-identified amy be natural or modified substances, ligands,receptors, eymzmes, etc., as the case may be, of Response regulator polypeptides and polunucleoties; or may be structual or functioal memetics thereof (see Coligan et al., *Cruuent Protocols in Innumolog* 1(2):Chapter 5 (1991)).

The screening methods may simply measure the binding of a candidate compound to the polypeptide or polynucleotide, or to cells or membranes bearing the poypeptide or polynucleotide, or a fusion protein of the polypeptide by means of a lable directly or indirectly associated with the candidate compound. Alternatively, the screening method may involve competition with a labeled competitor. Futher, these screening methods may test whether the canidate compound results in a signal generated by activation or inhibition of the polypeptide or poluncleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agoinst or ingibitor, by testing whether the candidate compound results in inhibition of activation of the polypeptide or polynucleotide, as the case may be. Further, the screening methods may simply comprise the steps of mixing a cadidate compound with a solution containing a polypeptide or polynucleotide of the present invention, to form a mixture, measuring Response regulator polypeptide and/or polynucleotide activity in the mixture and comparing the Response regulator polypeptide and/or polynucleotide activity of the mixture to a standard. Fusion proteins, such as those made from Fc portion and Response regulator polypeptide, as herinbefore described, can be used for high-thoughput screening assays to identify antagonists of the polypeptide of the present invention, as well as of phylogenetically and and/or functionally related polypeptides (see D. Bennett et al., *J Mol Recognition,* 8:52–58 (1995); and K. Johnson et al., *J Biol Chem,* 270 (16):9459–9471 (1995)).

The polynucleotides, polypeptides and antibodies that bind to and/or interact with a polypeptide of the present invention may also be used configure screening methods for detecting the effect of added compounds on the production of mRNA and/or polypeptide in cells. For example, an ELISA assay may be contructed for measuring secreted or cell associated levels os pplypeptide using monoclonal and polyclonal antibodies by standard methods known in the art. This can be used to discover agents which may inhibit or enhance the production of polypeptide (also called anatgonist or agonist, respectively) from suitably manipulated cells or tissues.

The invention also provides a method of screening compounds to identify those which enhance (agonist) or block (antagonist) the action of Response regulator polypeptides or polynucleotides, particularly those compounds that are bacteristatic and/or bactericidal. The method of screening may involve hihg-throughput techniques. For example, to screen for agonists or anagonists, a syumthetic reaction mix, a cellular compartment, such as a membrane, cell envelope or cell wall, or a preparation of any thereof, comprising Response regulator polypeptide and a labled substrate or ligand of such polypeptide is incubated in the abesence or the presence of a candidate molecule that may be a Response regulator agonist or antagonist. The ability of the cadidate molecule to agonize or anagonize the Response regulator polypeptide is reflected in decreased binding of the labled ligand or decreased production of product from such substrate. Molecules that bind gratutiously, i.e., without inducing the effects of Response reglator polypeptide are most likely to be good anagonists. Molecules that bind well and, as the case maybe, increase the rate of product production from substrate, increase signal transcuction, or increse chemical channel activity are agonists. Detectionof the rate or level of, as the case may bve production from substrate, signal transduction, or chemical channel activity may be enhanced by using a reporter system. Reporter systems that may be useful in this regarad inluce but are not limited to colormetric, labeled substrate converted intoproduct, a reporter gene that is responsive to changes in Response regulator polynucleotide or polypeptide activity, and binding assays known in the art.

Polypeptide of the invention may be used to identify membrance bound or soluble receptors, if any, for such polypeptide, through standard redeptor binding techniques known in the art. These techniques include, but are not limited to, ligand binding an crossslinking assays in which the polypeptide is labeled with a radioactive isitope (for instance, $^{125}I$), chemically modified (for instanc, biotinylated), or fused to apeptide sequence suitable for detection or purification, and incubated with a source of the putative receptor (e.g. cells, cell membranes, cell supernatants, tissue extracts, bodily materials). Other methods include biophysical techniques such as surface plasmon resonance and spectroscopy. These screening merthods may also be used to identify agonists and antagonists of the polyptide which compete with the binding of the polypeptide to its receptor(s), if any. Standard methods for conducting such assays are well understood in th art.

The fluorescence polariztion value for a fluoresecntly-tagged molecule depends on the rotational correlation time or tumbling rate. Protein compexes, such as formed by Response regulator polypeptide associating with another Response regulator polypeptide or other polypeptide, labled to comprise a fluorescently-labled molecule will have hihger polarization valuues than a fluorescently blabeled monomeric protein. It is preferred that this method be used to characterize small molecules that disrupt polypeptide complexes.

Flurescence energy transfermay also be used characterize small molecules that interfere with the fprmation of Response regulator polypepited dimers, timers, tetramers or higher order structures, or formed by Response regulator polypeptide bound to another polypeptide. Respones regulator polypeptied can be labled with both a donor and acceptor fluorophre. Upon micing of the two labled species and excitation of the donor fluorophore, fluorescence energy transfer can be detecrted by observing fluorescence fo the acceptor. Compounds that block demeriztion will inhibit flourescence energy tranfer.

Surface plasmon resonance cna be used to monitor the effect of small molecules on Response regulator polypeptide self-association as well as an assocication or Respones regulator polypeptide and another polypeptide or small molecule. Response regulator polypeptide can be coupled to sensor chaip at low site density such that covalently bound moecules will be monomeric. Solutionprotein can then passed over the Response regulator polypeptide -coated surface and specific binding can be detected in real-time by monitoring the change in resonance angle caused by a change in local refractive index. This technique can be used to characterize the effect of small molecules on kinetic rates and equilibrium binding constants for Response regulator polypeptide self-association as well as an association of Response regulator polypeptide and another polypeptide or small molecule.

A scintillation proximity assay may be used to characterize the interaction between an association of Response regulator polypeptide with another Response regulator polypeptide or a different polypeptide. Response regulator polypeptide can be coupled to a scintillation-filled bead. Addidtion of radir-labled Resonse regulator polypeptide results in binding wher the radioactive source molecule is in close proximity to the scintillation fluid. Thus, singal is emtted upon Response regulato polypeptide binding and compounds that prevent Response regulator polypeptide self-association or an assocation of Response regulator polypeptide and another polypeptide or small molecule will diminish signal.

ICS biosensors have been described by AMBRI (Australian Membrane Biotechnology Research Intitute). They couple the self-association of macromolecules to the closing of gramacidin-facilitatedion channels in suspended membrance bilayers and hence to a measurable change in the admittance (similar to impedence) of the biosensor. This approach is linear over six decades of admittence change and is ideally suited for large scale, high through-put screening of small molecule combinatorial libraries.

In other embodiments of the invention there are provide methods for identifying compounds which bind to or otherwise interact with and ingibit or activate or expression of a polypeptide and/or polynucleotide of the invention comprising: contacting a polypeptide and/or polynucleotide of the invention with a compond to be screened under conditions to permit binding to or other interaction between the compound and the polypeptide and/or polynucleotide to assess the binding to or othe interaction with the compound, such binding or interaction preferably being associated with a second component capable of providing a detectable signal in response to the binding or interaction of the polypeptide and/or polynucleotide with the compound; and dtermining whether the compound binds to or otherwise interacts with and activates or inhibits an activity or expression of the polypeptide and/or polynucleotide by detcting the presence or absence fo a signal geneated from the binding or interaction of the compound with the polypeptide and /or polynucleotide.

Another example of an assay for Response regulator agonists is a competitive assay that combines Response regulator and a protential agonist with Response regulator- binding molecules, recombinant Response regi;atpr bomdomg molecules, natural substarates or ligands, or substrate or ligand mimetics, under appropriate conditions for a competitive inhibiton assay. Response regulator can be labled, such as by radioactivity or a colormetric compound, such that the number of Response regulator molecules bounds to a binding molecule or converted to product can be determined accurately to assess the effectiveness of the potential antagonist.

Potential anagonist includs, among others, small organic molecules, peptides polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same site on a binding molecule, such as a binding molecule, without incucing Response regulator-induced activities, thereby preventing the action or expression of Response regulator polypeptides and/or polynucleotides by excluding Response regulator polypeptides and/or pounucleotides from binding.

Potential antagonists include a small moecule that binds to and occupies the binding site of the polypeptide thereby preventing binding to cellular binding molecules, such that normal biologivcal activity is prevented. Examples of smale molecules include but are not limited to small organic molecules, peptides or peptide-like molecules. Other potential anatagonists include antisense molecules (see Okano, *J. Neurocem.* 56: 560 (1991); OLIGODEOXYNUCLEOTIDES AS ANTISENSE INHIBITORS OF GENE EXPRESSION, CRC Press, Boca Raton, Fla. (1988), for a description of these molecules). Preferred potential antagonists include componds related to and variants of Response regulator. Other examples of potential polypeptide antagonists include andtibodies or, in some cases, oligonucleotides or proteins which are closely related to the ligands, substrates, receptors, enzymes, etc., as the case my be, of the polypeptide, e.g., a fragment of the liagands, subtractes, receptors, enzymes, etc., or small molecules which bind to the polypeptide of the presnt invention but do not elicit a repsonse, so that the activity of the polypeptide is prevented.

Certain of the polypeptides of the invention are biominetics, functional mimetics of the natural Response regulator polypeptide. These funtional memetics may be used for, among other things, antagonizing the activity of Response regulator polypeptide or a antigen or immunogen in a manner described elsewhere herein. Funtional mimetics of the polypeptiedes of the invention inlcude but are not limited to truncated polypeptides. For example, preferred functional memetics include, a polypeptide comprising the polypeptide sequence set forth in SEQ ID NO:2 lacking 20, 30, 40, 50, 60, 70 or 80 amino-or carboxy-terminal amino acid residues, including fusion proteins comprising one or more of these truncated sequences. Polynuleotides encoding each of these functional mimetics may be used as expression cassettes to express each mimetiv polypeptide. It is preferred that these cassettes comprise 5' and 3' restriction sites to allow for a convenient to ligate the cassettes together when disired. It is further preferred that these cassettes comprise gene expression signals known in the art or described elsewhere herein.

Thus, in another aspect, the present invention relates to a screeening kit for identifying agonists, anagonists, ligands, receptors, substrates, enzymes, etc. for a polypepetide and/or polynucleotide of the present invetion; or compounds which decrease or enhance the production of such polypeptides and/or polynucleotides, which comprises: (a) a polypeptide and/or a polynucleotide to the present invention; (b) a recombinant cell expressing a polypeptide and/or polynucleotide of the present invention; (c) a cell membrane expressing a polypeptide and/or polyncleotide of the present invention; or (d) antibody to a polypeptide and/or plyncleotide of the present invention; which polypeptide is preferably that of SEQ ID NO:2, and which polyncleotide is preferably that SEQ ID NO:1.

It will be appreciated that in any such kit, (a), (b), (c) or (d) may comprise a substantial component.

It will be readily appreciated by the skilled artisan that a plypeptide and/or polynucleotide of the present invention may also be used in a method for the structure-based design of an agonist, antagonist or inhibitor of the polypeptide and/or polynucleotide; by:(a) determining in the first instance the three-dimensional structure of the polypeptide and/or polynucleotide, or complexes thereof;(b) deducing the three-diemensional structures for the likely reactive site(s); binding site(s) or motif(s) of an agonist, antagonist or inhibitor; (c) synthesizing candidate compounds that are predicted to bind to react with the decuced binding site(s), reactive site(s); and/or motif(s); and (d) testing whether the candidate compounds are indeed agonists, antagonists or inhibitors. It will be further appreciated that this will normally be an iterative process, and this iterative process may be performed using automated and computer-controoled steps.

In a further aspect, the present invention provides methods of treating abnormal conditions such as for instance a Disease, related to either an excess of, an under-expression of, an elevated activity of, or a decresed activity of Response regulator polypeptide and/or polynucleotide. If the expression and/or activity of the polypeptide and or polynucleotide is in excess, several approaches are avialble. One approcah comprises administering to an indivdual in need thereof an inhibitor compound (antagonist) as herein described, optionally in combination with a pharmaceutically acceptable carrier, in an amount effective to inhibit the functon and/or expression of the polypeptide and/or polynucleotide, such as, for example, by blocking the bindiing of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragements of the Response regulator polypepetide and/or polypeptide.

In a further aspect, the present invention reates to genetically enginerred soluble fusion protiens comprising a polypeptide of the present invention, or a fragement thereof, and various portions of the conatant regions of heavy of light chains of immunoglobulins of various subclasses (IgG, IgM, IgA, IgE). Preferred as an immunoglobulin is the constant part of the heavy chain of human IgG. particularly IgG1, where fusion takes place at the hinge region. In a particular embodiment, the Fc part can be removed simply bu incorporation of a cleavage sequence which can be cleaved with blood clothing factor Xa. Furthermore, this invention relates to processes for the prepeartion of these fusion proteins by genetic engineering, and to the use thereof for drug secreening, diagnosis and theapy. A further aspect of the invention also realtes to polynucleotides encoding such fusion proteins. Examples of fusion protein technology can be found in Internatonl Patent Application Nos. W094/29458 and W094/22914.

In still another approach, expression of the gene encoding endogenous Response regulator polypeptide can be inhibied using expression blocking techniques. This blocking maybe targeted against may step in gene expression, byt is preferably targeted against transcription and/or translation. An examples of a know technique of this sort involve the use of antisense sequences, either internally generated or separately adminstered (see, for example, O'Connor, *J Neurochem* (1991) 56:560 in Oligodeoxynucleotides as Angisense Inhibotors of Gene Expression, CRC Prss, Boca Raton, Fla. (1988)). Alternatively, olgionucleoties which form triple helices with the gene can be supplied (see, for example, Lee et al., *Nucleic Acids Res* (1979) 6:3073; Cooney et al., *Sceince* (1988) 241:256; Dervan et al., *Science* (1991) 251:1360). These oligomers can be administered per se or the relevant oligomers can be expressed in vivo.

Each of the polynucleotide sequences provided herein may be used in the discovery and development of antibacterial commonds. The encorded protein, upon expression, can be used as a target for the screening of antibacterial drugs. Additionally, the polynucleotide sequences encoding the amino terminal regions of the encoded protein or Shine-Delgarno or other translation facilitating sequences of the respective mRNA can be used to contruct antisense equences to control the expression of the coding sequence of interest.

The invention also provides the use of the polypeptide, polynucleotide, agonist or antagonist of the invention of interfere with the initial physical interaction between a pathogen or pathogens and eukaryotic, preferably mammalian, host responsible for sequelae of infection. In particular, the molecules of the invention may be used: in the prevention of adhension of bacteria, in particular gram positive and/or gram negative bacteria, to eukayotic, preferably mammalian, extracellular matrix proteins on in-dewlling devices or to extracellular matrix proteins in wounds; to block bacterial adhesion between eukaryotic, preferably mammalian, extracellular matrix proteins and bacterial Response regulator proteins that mediate tissue damage and/or; to block the normal progression of pathogenesis in infections intiatted other than by the implantation of indwelling devices or by other surgical techniques.

The invention provides a method of screening drugs to identify those which: i) interfere with the interaction of the response regulator with a histidine kinase, the method comprising incubating the response regulator with histidine kinase in the presence of the drug and measuring the ability of the drug to block this intraction; ii) interfere with the ablilty of the response regulator to catalyse the transfer of phosphate group from the histidine kinase to itself, the method comprising incubating the response regulator with drug and measuring the ability of the response regulator to catalyse the removal of phosphate from phossphorylated histidine kinase; and/or iii) interfere with the ability of the molecule to autodephosphorylate itself once the phosphate had been transfered, the method comprising incubating the phosphorylated response regulator with drug and measuring the ability of the response regulator to catalyse the autodephosphorylation.

The histidine kinase is preferably the cognate histidine kinase of the rewponse regulator, or another histdine kinase which is capable of acting as a substrate for the response regulator, and may be from *Streptococcus pneumoniae* or another microorganism e.g. *Bacillus* Polypeptide and polynucleotide sequences of the cognate kinase of the Response Regulator of the invention are set forth in Table 1(E and F). This novel histidine kinase shows 21% identity to the LytS protein form *Bacillus Subtilis*.

In accordance with yet another aspect of the invention, there are provided Response regulator agonists and antagonists, preferably bacteristatic or bactericidal agonists and antagonists.

The antagonists and agonists of the invention may be employed, for instance, to prevent, inhibit and/or treat diseases.

*Helicobater pylori* (herein "*H. pylori*") bacteria infect the stomachs of over one-third of the world's population casuing stomach cancer, ulcer, and gastritis (International Agency for Research on Cancer (1994) *Schistorsomes, Liver Flukes and Helicobacter Pylori* (International Agency for Research on Caner, Lyon France, http://www.uicc.ch/ecp/ecp2094.htm). Moreover, the International Agency for Researh on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of Response regulator polypeptides and/or polynucleotides) found using screens provided by the invention, or known in the art, partivularly narrow-spectrum anitiotics, should be useful in the treatment of *H. pylori* infection. Such treatment should decrease the advent of *H. pylori*-induced cancers, such as gastrointestinal carcinoma. Such treament should also prevent, inhibit and/or cure gastric ulcers and gastritis.

Vaccines

There are provided by the invention, products, compositons and methods for assessing Response regulator expression, treating disease, assaying genetic variation, and administering a Response regulator polypeptide and/or polynucleotide to an organism to raise an immunlological response against a bacteria, especially a *Strptococcus pneumoniae* bacteria.

Another aspcet of the invention relates to a method for inducing an immunological response in an individual, particularly a mammal which comprises inoculating the individual with Response regulator polynucleotide and/or polypeptide, or a fragement or bariant thereof, adequate to produce antibody and/ or T cell immune respones to protct said induvidual from infection, particularly bacterial infection and most particularly *Streptococcus pneumoniae* infection. Also prvided are methods whereby such immunological response slows bacterial replication. Yet another aspect of the invention relates to a method of inducing immunological response in an individual with comprises delivering to such individual a nucleic acid vector, sequence or ribozyme to direct expression of regulator polynucleotide and/or polypeptide, or a fragment or a variant thereof, for expressing Response regulator polynucleotide and/or polypeptide, or a fragement or a variant therof in vivo in order to induce an immunological response, such as, to produce antibody and/or T cell immune respones, including, for example, cytokin-producing T cell or cytotoxic T cells, to protect said individual, preferably a human, from diseas, whether that disease is already establihed within the invdividual, or not. One example of administering the gene is by accelerating it into the desired cells as a coating on particles or otherwise. Such mucleic acid vector may comprise DNA, RNA, a ribozyme, a modified nucleic acid, a DNA/RNA hybird, a DNA-protein complex or as RNA-protein complex.

A further aspect of the invention relates to an immunological composition that when introduced into the individual, perferably a human, capable of having induced within it an immunological response, induces an immunological response in such individual to a Response regulator polynucleotide and/or polypeptide encoded therefrom, wherein the compostion comprises a recombinant Response regularto polynucleotide and/or polypeptide endcode thereform and/or comprises DNA and/or RNA which encodes and expresses an antigen of said Response regulator polynucleotide, polypeptide encoded therefor, or other polypeotide of the invention. The immunological response may be used therapeutically or prophyactically and may take the form of anibody immunity and/or cellular immunity, such as cellular imminity arising form CTL of CD4+ T cells.

A Response regulator polypeptide or a fragment thereof may be fused with co-protein or chemical moiety which may or may not by itself produce antibodies, but which is capable of stabilizing the first protein and producing a fused or modified protein which will have antigentic and/or immunogenic properties, and preferably protective properties. Thus fused recombinant protein, perferably further comprises an antigenic co-protein, such as lipoprotein D from *Hemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalizes stimulation of the immune system of the organism receiving the protein. The co-protein may be attached toeither the amino- or carboxy-teminus of the first protein.

Provided by this invention are compositions, particularly vaccine compositions, and methods comprising the polypeptides and/or polynuceotides of the invention and immunostimulatory DNA sequences, such as those decribed in Sato, Y. et al. *Science* 273: 352 (1996).

Also, provided by this invention are methods using the decribed polynucleotide or particular fragments thereof, which have been shown to encode non-variable regions of bacterial cell surface proteins, in polynucleotide contructs used in such genetic immunization experiments in animal modelof infection with *Streptococcus pneumoniae*. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Steptococcus pneumoniae* infecetion, in mammals, particularly humans.

A polypeptide of the invention may be used as an antigen for vaccination of a host to produce specific antibodies which protect against invasion of bacteria, for example by blocking adherence of bacteria to damaged tissue. Examples of tissue damage include wounds in skin or connective tissue caused, for example, by mechanical, chemical, thermal or radiation damage or by implantation of indwelling devices, or wounds in the mucous membranes, such as the mouth, throat, mammary glands, urethra or vagina.

The invention also includes a vaccine formulation which comprises an immunogenic recombinant polypeptide and/or polynucleotide of the invention together with a suitable carrier, such as a pharmaceutically acceptable carrier. since the polypeptides and plynucleotides may be broken down in the stomach, each is preferably administered parenterally, including, for example, administration that is subcutaneous, intramuscular, intravenous, or intradermal. Formulations suitble for parenteral administration include equeous and non-aqueous sterile injection solutions which may contain anti-oxidants, buffers, bacteristatic compounds and solutes which render the formulation isotonic with the bodily fluid, preferably the blood, of the individual; and equeous and non-aqueous suspenisons which may include suspending agents or thickening agents. The formulations maybe presented in unit-does or multi-does container, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as iol-in water systems and other systems known in the art. The dosage will depend on the specific activity of the vaccine and can be readily determinied by routine experimentation.

While the invention has been described with reference to certain Response regulator polypeptides and polynucleotides, it is to be understood that this covers fragements of the antuarally occurring polypeptides and polyncleotides, and sumilar polypeptides and polynucleotides with additions, deletions or substitutions which do not substantially affect the immunogenic properties of the recombinant polypeptides or polynucleotides.

Compositions, Kits and administration

In a further aspect of the invention there are provided compositions comprising a Response regualtor polynucleotide and/or a Response regulator polypeptide for a administration to a cell or to a mulicellular organism.

The invention also relates to compositions comprising a polynucleotide and/or a polypeptides discussed herein or their agonists or antagonists. The polypeptides and polynucleotides of the invention may be employed in combination with a non-sterile or sterile carrirer or carriers for use with cells, tissuse or organisms, such as a phamaceutical carrier suitable for administration to an inndividual. Such compropsitions comprise, for instance, a media additive or a therapeutically effective amount of a polypeptide and/or polynucleotide of the invention and a phamaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone of in conjunction with other compounds, such as therepeutic compounds.

The pharmaceutical compositions maybe adminsitered in any effective, convenient manner including for instance, administration by topical, oral, anal, vaginal, intravenous, intraperitioneal, intramuscular, subcutaneous, intransal or intradermal routes amoung others.

In therapy or as a prophylactic, the active agent may be adimistered to an individual as an injectable composition, for example as a sterile equeous dispersion, preferable isotonic.

Alternatively the composition may be formulated for topical application for example in the form of ointments, creas, lotions, eye ointments, eye drops, ear drops, mouthwash, impregnated dressings and sutures and aerosols, and may contain appropirate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to abouot 98% by weight of the formulation; more usually they will consitute up about *80%* by weight of the formulation.

In a further aspect, the present invention provides for phamaceutical compositions comprising a therepeutically effective amount of a polypeptide and/or polynucleotide, such as the soluble form of a polypeptide and/or polynucleotide of the present invention, agonist or antagonist peptide or small moulecule compound, in combination with a phamaceutically acceptable carrier or excipient. Such carrier include, but are not limited to saline, buffered saline, dextrose, water, glycerol, ethanol, and combinations thereof. The inventon further relates to pharmaceutical packs and kits comprising one or more containers filled with one or more of the ingredients of the aformentioned compostions of the invention. Polypeptides, polynucleotides and other compounds of the present inveintion may be employed alone or in conjunction with other compounds, such as theapeutic compounds.

The compostition will be adapted to the route of administration, for instance by a systemic or an oral route. Preferred forms of systemic admainistration include injection, typically by intravenous injection. Other injection routes, such as subcutaneous, intramuscular, or intraperitoneal, can be used. Althernative means for systemic administration include transmucosal and transdermal administration using penetrants such as bile sats or fusidic acids or other detergents. In addition, if a polypeptide or other compounds of the present invention can be formulated in an enteric or an encapsulated formulation, oral administration may also be possible. Administration of these compounds may also be topicla and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitble for an individual and will very with the age, weihgt and response of the particular individual. The above dosages are exemplary of the average case. There can, of course, be indivadual instances where higher or lower dosage ranges are merited, and such are within the scope of the invention.

In-dwelling devices include surgical implants, prosthetic devices and catheters, i.e., devices that are introduced to the body of an individual and remain in position for an extended time. Such devices include, for example, artifical joints, heart valves, pacemarkers, vascular grafts, vascular catheters, cerebropinal fluid shunts, urinary catheters, continuous ambulatory peritioneal dislyisi (CAPA) catheters.

The composition for the invention may be administered by injection to achieve a systemic effect against relevant bacteria shortly before inertion of an in-dwelling device. Treatment may be continued after surgry during the in-body time of the device. In addition, the composition could also be used to broaden perioperative cover for amy surgical technique to prevent bacterial wound infections, especially *Streptococcus pneumoniae wound infections*.

Many orthopedic surgeouns consider that humans with prothetic joints should be considered for antibiotic prophylaxis before dental tretment that could produce a bactermia, Late deep infection is a serious complication sometimes leading to loss of the prosthetic joint and is accompanied by significant morbidity and mortality. It may therefor be possible to extend the use of the active agent as a replacement for prophylactic antibiotics in this situation.

In addition to the theraphy described above, the compositions of this invention may be used generally as a wound treatment agent to prevent adhesion of bacteria to matix proteins exposed in wound tissue and for prophylactic use in dental treatment as an alternative to, or in conjunction with, antibiotic prophylaxis.

Alternatively, the compostion of the ivention may be used to bathe an indwelling device immediately befor insertion. The active agent will preferably be present at a concentration of 1μg/ml to 10mg/ml for bathing of wounds or indwelling devices.

A vaccine composition is conveiently in injectable form. Conventional adjuvants may be employed to enhance the immune response. A suitble unit dose for vaccination is 0.5–5 microgram/kg of antigen, and such dose is preferably administered 1–3 times and with an interval of 1–3 weeks. With the incated dose range, no adverse toxicological effects will be observed with the compounds of the invention which would preclude their administration to suitable individuals.

Sequence Databases, Sequences in a Tangible Medium, and Algorithms

Polynucleotide and polypeptide sequences form a baluable informatin resource with which to determaine their 2- and 3-dimensional structures as well as to identify fruther sequences of similar homology. These approaches are most easily facilatted by storing the sequence in a computer readable medium and them using the stored data in a known macromolecular structure program or to search a sequence database using well known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithms," and in claims related to this section, the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms and in claims related thereto, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. For example, a computer readable medium is provided comprising and having stored thereon a member selected from the group consisting of: a polynucleotide comprising the sequence of a polynucleotide of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of the sequences comprises the sequence of a polypeptide sequence of the invention; a data set representing a polynucleotide sequence comprising the sequence of polynucleotide sequence of the invention; a data set representing a polynucleotide sequence encoding a polypeptide sequence comprising the sequence of a polypeptide sequence of the invention; a polynucleotide comprising the sequence of a polynucleotide sequence of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of said sequences comprises the sequence of a polypeptide sequence of the invention; a data set representing a polynucleotide sequence comprising the sequence of a polynucleotide sequence of the invention; a data set representing a polynucleotide sequence encoding a polypeptide sequence comprising the sequence of a polypeptide sequence of the invention. The computer readable medium can be any composition of matter used to store information or data, including, for example, commercially available floppy disks, tapes, chips, hard drives, compact disks, and video disks.

Also provided by the invention are methods for the analysis of character sequences or strings, particularly genetic sequences or encoded genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, nucleic acid base trimming, and sequencing chromatogram peak analysis.

A computer based method is provided for performing homology identification. This method comprises the steps of providing a first polynucleotide sequence comprising the sequence a polynucleotide of the invention in a computer readable medium; and comparing said first polynucleotide sequence to at least one second polynucleotide or polypeptide sequence to identify homology.

A computer based method is also provided for performing homology identification, said method comprising the steps of: providing a first polypeptide sequence comprising the sequence of a polypeptide of the invention in a computer readable medium; and comparing said first polypeptide sequence to at least one second polynucleotide or polypeptide sequence to identify homology.

A computer based method is still further provided for polynucleotide assembly, said method comprising the steps of: providing a first polynucleotide sequence comprising the sequence of a polynucleotide of the invention in a computer readable medium; and screening for at least one overlapping region between said first polynucleotide sequence and at least one second polynucleotide or polypeptide sequence.

A computer based method is still further provided for polynucleotide assembly, said method comprising the steps of: providing a first polypeptide sequence comprising a polypeptide of the invention in a computer readable medium; and screening for at least one overlapping region between said first polypeptide sequence and at least one second polynucleotide or polypeptide sequence.

In another preferred embodiment of the invention there is provided a computer readable medium having stored thereon a member selected from the group consisting of: a polynucleotide comprising the sequence of SEQ ID NO:1 OR 3; a polypeptide comprising the sequence of SEQ ID NO:2 or 4; a set of polynucleotide sequences wherein at least one of said sequences comprises the sequence of SEQ ID NO:1 or 3; a set of polypeptide sequences wherein at least one of said sequences comprises the sequence of SEQ ID NO:2 or 4; a data set representing a polynucleotide sequence comprising the sequence of SEQ ID NO:1 or 3; a data set representing a polynucleotide sequence encoding a polypeptide sequence comprising the sequence of SEQ ID NO:2 or 4; a polynucleotide comprising the sequence of SEQ ID NO:1 or 3; a polypeptide comprising the sequence of SEQ ID NO:2 or 4; a set of polynucleotide sequences wherein at least one of said sequences comprises the sequence of SEQ ID NO:1 or 3; a set of polypeptide sequences wherein at least one of said sequences comprises the sequence of SEQ ID NO:2 or 4; a data set representing a polynucleotide sequence comprising the sequence of SEQ ID NO:1 or 3; a data set representing a polynucleotide sequence encoding a polypeptide sequence comprising the sequence of SEQ ID NO:2 or 4. A further preferred embodiment of the invention provides a computer based method for performing homology identification, said method comprising the steps of providing a polynucleotide sequence comprising the sequence of SEQ ID NO:1 or 3 in a computer readable medium; and comparing said polynucleotide sequence to at least one polynucleotide or polypeptide sequence to identify homology.

A still further preferred embodiment of the invention provides a computer based method for performing homology identification, said method comprising the steps of: providing a polypeptide sequence comprising the sequence of SEQ ID NO:2 or 4 in a computer readable medium; and comparing said polypeptide sequence to at least one polynucleotide or polypeptide sequence to identify homology.

A further embodiment of the invention provides a computer based method for polynucleotide assembly, said method comprising the steps of: providing a first polynucleotide sequence comprising the sequence of SEQ ID NO:1 or 3 in a computer readable medium; and screening for at least one overlapping region between said first polynucleotide sequence and a second polynucleotide sequence.

A further embodiment of the invention provides a computer based method for performing homology identification, said method comprising the steps of: providing a polynucleotide sequence comprising the sequence of SEQ ID NO:1 or 3 in a computer readable medium; and comparing said polynucleotide sequence to at least one polynucleotide or polypeptide sequence to identify homology.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

GLOSSARY

The following definitions are provided to facilitate understanding of certain terms used frequently herein.

"Antibody(ies)" as used herein includes polyclonal and monoclonal antibodies, chimeric, single chain, and humanized antibodies, as well as Fab fragments, including the products of an Fab or other immunoglobulin expression library.

"Antigenically equivalent derivative(s)" as used herein encompasses a polypeptide, polynucleotide, or the equivalent of either which will be specifically recognized by certain antibodies which, when raised to the protein, polypeptide or polynucleotide according to the invention, interferes with the immediate physical interaction pathogen and mammalian host.

"Bispecific antibody(ies)" means an antibody comprising at least two antigen binding domains, each domain directed against a different epitope.

"Bodily material(s) means any material derived from an individual or from an organism infecting, infesting or inhabiting an individual, including but not limited to, cells tissues and waste, such as, bone, blood, serum, cerebrospinal fluid, semen, saliva, muscle, cartilage, organ tissue, skin, urine, stool or autopsy materials.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid, "Fusion protein(s)" refers to a protein encoded by two, often unrelated, fused genes or fragments thereof. In one example, EP-A-0464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see e.g., EP-A 0232262]. On the other hand, for some uses it would be desirable to be able to delete the Fc part after the fusion protein has been expressed, detected and purified.

"Host cell(s)" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case may be, as determined by comparing the sequences. In the art, "identity" also means the degree of sequence relatedness polypeptide or polynucleotide sequences, as the case may be, as determined by the match between strings of such sequences. "Identity" can be readily calculated by known methods, including but not limited to those described in (*Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and *Sequence Analysis Primer,* Gribskov, M. and Devereux, J., eds., M Stockton Press, New York, 1991; and Carillo, H., and Lipman, D., SIAM *J. Applied Math.,* 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual,* Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following: Algorithm: Needleman and Wunsch, J. Mol Biol. 48: 443–453 (1970) Comparison matrix: BLOSUM62 from Hentikoff and Hentikoff, Proc. Natl. Acad. Sci. USA 89:10915–10919 (1992).

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following: Algorithm: Needleman and Wunsch, J. Mol. Biol. 48: 443–453 (1970)
Comparison Matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NO:1, wherein said polynucleotide sequence may be identical to the reference sequence of SEQ ID NO:1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between the terminal positions, interspersed either individually among the nucleotides in the reference sequence or in one or more contiguous groups within the reference sequence, and wherein said number of nucleotide alterations is determined by multiplying the total number of nucleotides in SEQ ID NO:1 by the integer defining the percent identity divided by 100 and then subtracting that product from said total number of nucleotides in SEQ ID NO:1, or:

$$n_n \leq x_n - (x_n \cdot y),$$

wherein $n_n$ is the number of nucleotide alterations, $x_n$ is the total number of nucleotides in SEQ ID NO:1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:1, that is it may be 100% identical, or it may include up to a certain integer number of nucleic acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interposed either individually among the nucleic acids in the reference sequence or in one or more contiguous groups within the reference sequence. The number of nucleic acid alterations for a given percent identity is determined by multiplying the total number of nucleic acids in SEQ ID NO:1 by the integer defining the percent identity divided by 100 and then subtracting that product from said total number of nucleic acids in SEQ ID NO:1, or:

$$n_n \leq x_n - (x_n \cdot y),$$

wherein $n_n$ is the number of nucleic acid alterations, $x_n$ is the total number of nucleic acids in SEQ ID NO:1, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO:2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Immunologically equivalent derivative(s)" as used herein encompasses a polypeptide, polynucleotide, or the equivalent of either which when used in a suitable formulation to raise antibodies in a vertebrate, the antibodies act to interfere with the immediate physical interaction between pathogen and mammalian host.

"Immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

"Individual(s)" means a multicellular eukaryote, including, but not limited to a metazoan, a mammal, an ovid, a bovid, a simian, a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moraxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Shigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Steptococcus faecalis, Streptococcus faecium, Streptococcus durans, Neisseria gonorrheae, Neisseria meningitidis, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenze, Haemophilus aegyptius, Haemophilus parainfluenzae, Haemophilus ducreyi, Bordetella, Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsii* and *Chlamydia trachomitis*, (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis*, or *Candida albicans*.

"Polynucleotide(s)" generally refers to any polyribonucleotide or polydeoxyribonucleotide, which may be unmodified RNA or DNA or modified RNA or DNA. "Polynucleotide(s)" include, without limitation single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polynucleotide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyrogultamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, *PROTEINS—STRUCTURE AND MOLECULAR PROPERTIES,* 2nd Ed., T. E. Creighton, W. H. Freeman and Company, New York (1993) and Wold, F., Posttranslational Protein Modifications: Perspectives and Prospects, pgs. 1–12 in *POSTTRANSLATIONAL COVALENT MODIFICATION OF PROTEINS,* B. C. Johnson, Ed., Academic Press, New York (1983); Seifter et al., *Meth. Enzymol.* 182:626–646 (1990) and Rattan et al., *Protein Synthesis: Posttranslational Modifications and Aging,* Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Subtraction set" is one or more, but preferably less than 100, polynucleotides comprising at least one polynucleotide of the invention.

"Variant(s)" are the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so in that the sequences of the reference polypeptide and the variant are closely similar overall and, in many regions, identical. A variant and reference polypeptide may differ in amino acid sequence by one or more substituents, additions, deletions in any combination. A substituted or inserted amino acid residue may or may not be one encoded by the genetic code. The present invention also includes include variants of each of the polypeptide of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5-10, 1-5, 1-3, 1-2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain selection, Library Production and Sequencing

The polynucleotide having a DNA sequence given in Table 1 [SEQ ID NO:1 or 3] was obtained from a library of clones of chromosomal DNA of *Streptococcus pneumoniae* in *E. coli.* The sequencing data from two or more clones containing overlapping *Streptococcus pneumoniae* DNAs was used to construct the contiguous DNA sequence in SEQ ID NO:1. Libraries may be prepared by routine methods, for example: Method 1 and 2 below Total cellular DNA is isolated from *Streptococcus pneumoniae* 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and *E. coli* infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and *E. coli* infected with the packaged library. The library is amplified by standard procedures.

Example 2

Response regulator Characterization

The determination of expression during infection of a gene from *Streptococcus pneumoniae*

Excised lungs from a 48 hour respiratory tract infection of *Streptococcus pneumoniae* 0100993 in the mouse is efficiently disrupted and processed in the presence of chaotropic agents and RNAase inhibitor to provide a mixture of animal and bacterial RNA. The optimal conditions for disruption and processing to give stable preparations and high yields of bacterial RNA are followed by the use of hybridisation to a radiolabelled oligonucleotide specific to *Streptococcus pneumoniae* 16S RNA on Northern blots. The RNAase free, DNAase free, DNA and protein free preparations of RNA obtained are suitable for Reverse Transcription PCR (RT-PCR) using unique primer parts designed from the sequence of each gene of *Streptococcus pneumoniae* 0100993.

a) Isolation of tissue infected with *Streptococcus pneumoniae* 0100993 from a mouse animal model of infection (lungs)

*Streptococcus pneumoniae* 0100993 is grown either on TSA/5% horse blood plates or in AGCH medium overnight, 37° C., 5%$CO_2$. Bacteria are then collected and resuspended in phosphate-buffered saline to an A600 of approximately 0.4. Mice are anaesthetized with isofluorane and 50 ml of bacterial suspension (approximately 2×10⁵ bacteria) is administered intranasally using a pipetman. Mice are allowed to recover and have food and water ad libitum. After 48 hours, the mice are euthanized by carbon dioxide overdose, and lungs are aseptically removed and snap-frozen in liquid nitrogen.

b) Isolation of *Streptococcus pneumoniae* 0100993 RNA from infected tissue samples Infected tissue samples, in 2-ml cryo-storage tubes, are removed from −80° C. storage into a dry ice ethanol bath. In a microbiological safety cabinet the samples are disrupted up to eight at a time while the remaining samples are kept frozen in the dry ice ethanol bath. To disrupt the bacteria within the tissue sample, 50–100 mg of the tissue is transferred to a FastRNA tube containing a silica/ceramic matrix (BIO101). Immediately, 1 ml of extraction reagents (FastRNA reagents, BIO101) are added to give a sample to reagent volume ratio of approximately 1 to 20. The tubes are shaken in a reciprocating shaker (FastPrep FP120, BIO101) at 6000 rpm for 20–120 sec. The crude RNA preparation is extracted with cloroform/isoamyl alcohol, and precipitated with DEPC-treated/Isopropanol Precipitation Solution (BIO101). RNA preparations are stored in this isopropanol solution at −80° C. if necessary. The RNA is pelleted (12,000 g for 10 min.), washed with 75% ethanol (v/v in DEPC-treated water), air-dried for 5–10 min, and resuspended in 0.1 ml of DEPC-treated water, followed by 5–10 minutes at 55° C. Finally, after at least 1 minute on ice, 200 units of Rnasin (Promega) is added.

RNA preparations are stored at −80° C. for up to one month. For longer term storage the RNA precipitate can be stored at the wash stage of the protocol in 75% ethanol for at least one year at −20° C.

Quality of the RNA isolated is assessed by running samples on 1% agarose gels. 1×TBE gels stained with ethidium bromide are used to visualise total RNA yields. To demonstrate the isolation of bacterial RNA from the infected tissue 1×MOPS, 2.2M formaldehyde gels are run and vacuum blotted to Hybond-N (Amersham). The blot is then hybridised with a 32P-labelled oligonucletide probe, of sequence 5' AACTGAGACTGGCTTTAAGAGATTA 3' [SEQ ID NO:9], specific to 16S rRNA of *Streptococcus pneumoniae*. The size of the hybridising band is compared to that of control RNA isolated from in vitro grown *Streptococcus pneumoniae* 0100993 in the Northern blot. Correct sized bacterial 16S rRNA bands can be detected on total RNA samples which show degradation of the mammalian RNA when visualised on TBE gels.

c) The removal of DNA from *Streptococcus pneumoniae*-derived RNA

DNA was removed from 50 microgram samples of RNA by a 30 minute treatment at 37° C. with 20 units of RNAase-free DNAaseI (GenHunter) in the buffer supplied in a final volume of 57 microliters.

The DNAase was inactivated and removed by treatment with TRIzol LS Reagent (Gibco BRL, Life Technologies) according to the manufactured protocol. DNAase treated RNA was resuspended in 100 microlitres of DEPC treated water with the addition of Rnasin as described before.

d) The preparation of cDNA from RNA samples derived from infected tissue 3 microgram samples of DNAase treated RNA are reverse transcribed using a SuperScript Preamplification System for First Strand cDNA Synthesis kit (Gibco BRL, Life Technologies) according to the manufacturers instructions. 150 nanogram of random hexamers is used to prime each reaction. Controls without the addition of SuperScriptII reverse transcriptase are also run. Both +/−RT samples are treated with RNaseH before proceeding to the PCR reaction e) The use of PCR to determine the presence of a bacterial cDNA species PCR reactions are set up on ice in 0.2 ml tubes by adding the following components: 43 microlitres PCR Master Mix (Advanced Biotechnologies Ltd.); 1 microlitre PCR primers (optimally 18–25 basepairs in length and designed to possess similar annealing temperatures), each primer at 10 mM initial concentration; and 5 microlitres cDNA.

PCR reactions are run on a Perkin Elmer GeneAmp PCR System 9600 as follows: 2 minutes at 95° C., then 50 cycles of 30 seconds each at 94° C., 50° C. and 72° C. followed by 7 minutes at 72° C. and then a hold temperature of 20° C. (the number of cycles is optimally 30–50 to determine the appearance or lack of a PCR product and optimally 8–30 cycles if an estimation of the starting quantity of cDNA from the RT reaction is to be made); 10 microlitre aliquots are then run out on 1% 1×TBE gels stained with ethidium bromide, with PCR product, if present, sizes estimated by comparison to a 100 bp DNA Ladder (Gibco BRL, Life Technologies). Alternatively if the PCR products are conveniently labelled by the use of a labelled PCR primer (e.g. labelled at the 5'end with a dye) a suitable aliquot of the PCR product is run out on a polyacrylamide sequencing gel and its presence and quantity detected using a suitable gel scanning system (e.g. ABI Prism™ 377 Sequencer using GeneScan™ software as supplied by Perkin Elmer).

RT/PCR controls may include +/− reverse transcriptase reactions, 16S rRNA primers or DNA specific primer pairs designed to produce PCR products from non-transcribed *Streptococcus pneumoniae* 0100993 genomic sequences.

To test the efficiency of the primer pairs they are used in DNA PCR with *Streptococcus pneumoniae* 0100993 total DNA. PCR reactions are set up and run as described above using approx. 1 microgram of DNA in place of the cDNA.

Primer pairs which fail to give the predicted sized product in either DNA PCR or RT/PCR are PCR failures and as such are uniformative. Of those which give the correct size product with DNA PCR two classes are distinguished in RT/PCR: 1.Genes which are not transcribed in vivo reproducibly fail to give a product in RT/PCR; and 2.Genes which are transcribed in vivo reproducibly give the correct size product in RT/PCR and show a stronger signal in the +RT samples then the signal (if at all present) in −RT controls Based on these analyses it was discovered that this *Streptococcus pneumoniae* response regulator gene was transcribed in vivo.

Example 3

Essentiality of a Response regulator-Histidine kinase pair from *S. pneumoniae*.

An allelic replacement cassette is generated using PCR technology. The cassette typically consists of a pair of 500 bp chromosomal DNA fragments flanking an erythromycin resistance gene. The chromosomal DNA sequence are usually the 500 bp preceding and following the gene of interest. Attempts are made to introduce the allelic replacement cassette into *S. pneumoniae* R6 or *S. pneumoniae* 100993 by transformation. Competent cells are prepared according to published protocols. DNA is introduced into the cells by incubation of 500 ng of allelic replacement cassette with $10^6$ cells at 30° C. for 30 minutes. The cells are transferred to 37° C. for 90 minutes to allow expression of the erythromycin resistance gene. Cells are plated in agar containing 1 μg erythromycin per ml. Following incubation at 37° C. for 36 hours, any observed colonies are picked and grown overnight in Todd-Hewitt broth supplemented with 0.5% yeast extract. Typically, in positive control experiments carried out in parallel with target a non-essential gene, $10^2$–$10^3$ transformants containing the appropriate allelic replacement are obtained. If erythromycin resistant colonies are only observed in transformation experiments using S. pneumoniae R6, DNA from these cells are used to transform S. pneumoniae 100993. The transformation procedure is identical to that for S. pneumoniae R6 except that a competence stimulating heptadecapeptide (Havarstein et al., (1995) P.N.A.S. 92, 11140–11144) is added at a concentration of 1 μg/ml in the initial transformation mix. Mutants are selected by their ability to grow in agar containing 1 μg erythromycin per ml.

If no transformants are obtained in three separate transformation experiments, then the target gene is considered as being essential in vitro. However if colonies are obtained DNA is prepared from these cells and examined using diagnostic PCR. Oligonucleotides designed to hybridize to sequences within the allelic replacement cassette are used in conjunction with DNA primers hybridizing to chromosomal sequences outside the cassette to generate DNA products amplified by PCR of characteristic size. The chromosomal DNA is also subject to Southern analysis in order to verify that the appropriate chromosomal DNA rearrangement has occurred. In order to demonstrate that the mutation is stably maintained the defective strain is grown for many generations in the absence of selective pressure and then assayed for its ability to grow in the absence or presence of erythromycin.

Based on these analyses the response regulator and its cognate histidine kinase were shown to be essential when deleted together.

What is claimed is:

1. An isolated polypeptide comprising SEQ ID NO:2, wherein the isolated polypeptide exhibits response regulator activity.

2. A composition comprising the isolated polypeptide of claim 1 and a carrier.

3. The isolated polypeptide of claim 1, wherein the isolated polypeptide comprises a heterologous amino acid sequence fused to SEQ ID NO:2.

4. A composition comprising the isolated polypeptide of claim 3 and a carrier.

5. The isolated polypeptide of claim 1, wherein the isolated polypeptide consists of SEQ ID NO:2, wherein the isolated polypeptide exhibits response regulator activity.

6. A composition comprising the isolated polypeptide of claim 5 and a carrier.

7. An isolated polypeptide comprising a fragment of SEQ ID NO.2 comprising at least 50 consecutive amino acids of SEQ ID NO:2; wherein said fragment exhibits response regulator activity.

8. A composition comprising the isolated polypeptide of claim 7 and a carrier.

9. The isolated polypeptide of claim 7, wherein the isolated polypeptide comprises a heterologous amino acid sequence fused to the at least 50 consecutive amino acids of SEQ ID NO:2.

10. A composition comprising the isolated polypeptide of claim 9 and a carrier.

11. An isolated polypeptide comprising a fragment of SEQ ID NO:2 comprising at least 30 consecutive amino acids of SEQ ID NO:2; wherein said fragment exhibits response regulator activity.

12. A composition comprising the isolated polypeptide of claim 11 and a carrier.

13. The isolated polypeptide of claim 11, wherein the isolated polypeptide comprises a heterologous amino acid sequence fused to the at least 30 consecutive amino acids of SEQ ID NO:2.

14. A composition comprising the isolated polypeptide of claim 13 and a carrier.

15. An isolated polypeptide comprising a fragment of SEQ ID NO:2 comprising at least 50 consecutive amino acids of SEQ ID NO:2; wherein said fragment has the ability to generate antibodies to SEQ ID NO:2.

16. A composition comprising the isolated polypeptide of claim 15 and a carrier.

17. The isolated polypeptide of claim 15, wherein the isolated polypeptide comprises a heterologous amino acid sequence fused to the at least 50 consecutive amino acids of SEQ ID NO:2.

18. A composition comprising the isolated polypeptide of claim 17 and a carrier.

19. An isolated polypeptide comprising a fragment of SEQ ID NO:2 comprising at least 30 consecutive amino acids of SEQ ID NO:2; wherein said fragment has the ability to generate antibodies to SEQ ID NO:2.

20. A composition comprising the isolated polypeptide of claim 19 and a carrier.

21. The isolated polypeptide of claim 19, wherein the isolated polypeptide comprises a heterologous amino acid sequence fused to the at least 30 consecutive amino acids of SEQ ID NO:2.

22. A composition comprising the isolated polypeptide of claim 21 and a carrier.

* * * * *